United States Patent
Dixon et al.

(10) Patent No.: US 9,895,158 B2
(45) Date of Patent: *Feb. 20, 2018

(54) METHOD AND APPARATUS FOR ACCELERATED DISINTEGRATION OF BLOOD CLOT

(71) Applicant: University of Virginia Patent Foundation, Charlottesville, VA (US)

(72) Inventors: Adam Joseph Dixon, Charlottesville, VA (US); John Alexander Hossack, Charlottesville, VA (US)

(73) Assignee: University of Virginia Patent Foundation, Charlottesville, VA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/736,191

(22) Filed: Jun. 10, 2015

(65) Prior Publication Data

US 2015/0272601 A1   Oct. 1, 2015
US 2017/0360460 A9   Dec. 21, 2017

Related U.S. Application Data

(63) Continuation-in-part of application No. 14/063,830, filed on Oct. 25, 2013, now Pat. No. 9,526,922, which
(Continued)

(51) Int. Cl.
*A61B 17/22*   (2006.01)
*A61M 13/00*   (2006.01)
(Continued)

(52) U.S. Cl.
CPC .......... *A61B 17/2202* (2013.01); *A61B 8/12* (2013.01); *A61B 8/445* (2013.01);
(Continued)

(58) Field of Classification Search
CPC ...... A61B 17/2202; A61B 2017/22088; A61B 2017/22089; A61B 8/12; A61B 8/445;
(Continued)

(56) References Cited

U.S. PATENT DOCUMENTS 5,041,089 A   8/1991   Mueller et al.
5,117,831 A   6/1992   Jang et al.
(Continued)

FOREIGN PATENT DOCUMENTS

WO   WO1996036286   11/1996
WO   WO 2006/015091 A3   2/2006
(Continued)

OTHER PUBLICATIONS

International Search Report from PCT/US2015/04734 dated Jan. 11, 2016.
(Continued)

*Primary Examiner* — Michael Rozanski
(74) *Attorney, Agent, or Firm* — Robert J. Decker; Alan W. Cannon

(57) ABSTRACT

Systems and methods for treating a blood clot include a catheter to be inserted into a patient. The catheter is used to deliver low stability microbubbles toward the blood clot in the patient. A thrombolytic agent is delivered toward the blood clot, and ultrasonic energy is applied to the microbubbles to vibrate the microbubbles.

136 Claims, 13 Drawing Sheets

Related U.S. Application Data is a continuation of application No. 12/739,128, filed as application No. PCT/US2008/081189 on Oct. 24, 2008, now Pat. No. 8,622,911, application No. 14/736,191, filed on Jun. 10, 2015, which is a continuation-in-part of application No. 13/386,391, filed as application No. PCT/US2010/042783 on Jul. 21, 2010, now Pat. No. 9,237,898.

(60) Provisional application No. 61/000,632, filed on Oct. 26, 2007, provisional application No. 61/099,025, filed on Sep. 22, 2008, provisional application No. 62/049,338, filed on Sep. 11, 2014, provisional application No. 61/227,284, filed on Jul. 21, 2009, provisional application No. 61/253,435, filed on Oct. 20, 2009, provisional application No. 61/298,741, filed on Jan. 27, 2010.

(51) Int. Cl.
| | |
|---|---|
| *A61K 41/00* | (2006.01) |
| *A61B 8/00* | (2006.01) |
| *A61N 7/00* | (2006.01) |
| *A61K 49/22* | (2006.01) |
| *A61M 37/00* | (2006.01) |
| *A61B 8/12* | (2006.01) |
| *A61B 8/08* | (2006.01) |

(52) U.S. Cl.
CPC ........ *A61K 41/0028* (2013.01); *A61K 49/223* (2013.01); *A61M 13/00* (2013.01); *A61M 37/0092* (2013.01); *A61N 7/00* (2013.01); *A61B 8/481* (2013.01); *A61B 2017/22088* (2013.01); *A61B 2017/22089* (2013.01); *A61M 2205/3306* (2013.01); *A61M 2205/3379* (2013.01); *A61N 2007/0039* (2013.01); *A61N 2007/0043* (2013.01); *A61N 2007/0052* (2013.01)

(58) Field of Classification Search
CPC .. A61B 8/481; A61K 41/0028; A61K 49/223; A61M 13/00; A61M 2205/3306; A61M 2205/3379; A61M 37/0092; A61N 2007/0039; A61N 2007/0043; A61N 2007/0052; A61N 7/00
See application file for complete search history.

(56) References Cited

U.S. PATENT DOCUMENTS

| | | | |
|---|---|---|---|
| 5,222,970 A | 6/1993 | Reeves et al. | |
| 5,415,634 A | 5/1995 | Glynn et al. | |
| 5,447,503 A | 9/1995 | Miller et al. | |
| 5,558,092 A | 9/1996 | Unger et al. | |
| 5,577,505 A | 11/1996 | Brock-Fisher et al. | |
| 5,707,354 A | 1/1998 | Salmon et al. | |
| 5,755,707 A | 5/1998 | Miyagawa et al. | |
| 5,770,222 A | 6/1998 | Unger et al. | |
| 5,827,171 A | 10/1998 | Dobak et al. | |
| 5,868,708 A | 2/1999 | Hart et al. | |
| 5,941,870 A | 8/1999 | Jang et al. | |
| 6,352,683 B1 | 3/2002 | ten Cate | |
| 6,409,667 B1 | 6/2002 | Hossack | |
| 6,527,979 B2 | 3/2003 | Constantz et al. | |
| 6,565,601 B2 | 5/2003 | Wallace et al. | |
| 6,626,861 B1 | 9/2003 | Hart et al. | |
| 7,011,677 B2 | 3/2006 | Wallace et al. | |
| 7,078,015 B2 | 7/2006 | Unger | |
| 7,198,637 B2 | 4/2007 | Deshmukh et al. | |
| 7,341,569 B2 | 3/2008 | Soltani et al. | |
| 8,622,911 B2 | 1/2014 | Hossack et al. | |
| 9,237,898 B2* | 1/2016 | Hossack | A61B 8/12 |
| 2002/0044907 A1 | 4/2002 | Constantz et al. | |
| 2002/0082680 A1 | 6/2002 | Shanley et al. | |
| 2002/0169496 A1 | 11/2002 | Wallace et al. | |
| 2003/0163192 A1 | 8/2003 | Wallace et al. | |
| 2003/0181973 A1 | 9/2003 | Sahota | |
| 2003/0199820 A1 | 10/2003 | Constantz et al. | |
| 2003/0204171 A1 | 10/2003 | Kucharezyk et al. | |
| 2003/0206960 A1 | 11/2003 | Eversen et al. | |
| 2003/0207907 A1 | 11/2003 | Eversen et al. | |
| 2003/0220666 A1 | 11/2003 | Mirigian et al. | |
| 2004/0030250 A1 | 2/2004 | Stewart | |
| 2004/0077948 A1 | 4/2004 | Violante et al. | |
| 2004/0111145 A1 | 6/2004 | Serino et al. | |
| 2004/0126400 A1 | 7/2004 | Iversen et al. | |
| 2004/0158308 A1 | 8/2004 | Hogendijk et al. | |
| 2004/0236414 A1 | 11/2004 | Brar et al. | |
| 2004/0254635 A1 | 12/2004 | Shanley et al. | |
| 2005/0017725 A1 | 1/2005 | Murakami et al. | |
| 2005/0084538 A1 | 4/2005 | Dayton et al. | |
| 2005/0192556 A1 | 9/2005 | Soltani et al. | |
| 2006/0005876 A1 | 1/2006 | Gandiana et al. | |
| 2006/0078501 A1 | 4/2006 | Goertz et al. | |
| 2006/0161103 A1 | 7/2006 | Constantz et al. | |
| 2006/0189928 A1 | 8/2006 | Camus et al. | |
| 2006/0235501 A1 | 10/2006 | Igaki et al. | |
| 2007/0003528 A1 | 1/2007 | Consigny et al. | |
| 2007/0010577 A1 | 1/2007 | Lanza et al. | |
| 2007/0043389 A1 | 2/2007 | Shindelman et al. | |
| 2007/0049867 A1 | 3/2007 | Shindelman et al. | |
| 2007/0055132 A1 | 3/2007 | Camus et al. | |
| 2007/0055327 A1 | 3/2007 | Esch et al. | |
| 2007/0071683 A1 | 3/2007 | Dayton et al. | |
| 2008/0103443 A1 | 5/2008 | Kabrick et al. | |
| 2008/0243233 A1 | 10/2008 | Ben-Muvhar et al. | |
| 2009/0098168 A1* | 4/2009 | Hettiarachchi | B01J 13/04 424/400 |
| 2010/0049192 A1* | 2/2010 | Holtz | A61B 18/1492 606/41 |
| 2010/0331686 A1 | 12/2010 | Hossack et al. | |
| 2012/0209116 A1* | 8/2012 | Hossack | A61B 8/12 600/439 |
| 2012/0219727 A1* | 8/2012 | Gandhiraman | B01L 3/502707 427/563 |
| 2014/0142468 A1 | 5/2014 | Hossack et al. | |

FOREIGN PATENT DOCUMENTS

| | | |
|---|---|---|
| WO | WO 2006/015144 A1 | 2/2006 |
| WO | WO 2006/089243 A3 | 8/2006 |
| WO | WO 2008/057626 A3 | 5/2008 |
| WO | WO 2008/112870 A3 | 9/2008 |
| WO | WO 2008/115745 A3 | 9/2008 |
| WO | WO 2008/118737 A1 | 10/2008 |

OTHER PUBLICATIONS

Ingall: Stroke-incidence, mortality, morbidity and risk. J Insur Med 36(2):143-152 (2004).
Lloyd-Jones et al.: Heart disease and stroke statistics—2009 update. Circulation 119(3):480-486 (2009).
Marler: Tissue plasminogenactivator for acute ischemic stroke. N Engl J Med. 333:1581-1587 (1995).
Smith et al., Safety and efficacy of mechanical embolectomy in acute ischemic stroke: results of the MERCI trial. Stroke. Jul. 2005;36(7):1432-8. Epub Jun. 16, 2005.(2005).
Alexandrov et al: CLOTBUST Investigators: Ultrasound-enhanced systemic thrombolysis for acute ischemic stroke. N Engl J Med 351:2170-2178, (2004)
Alexandrov et al.: A pilot randomized clinical safety study of sonothrombolysis. Stroke 39:1464-1469, (2008).
Dinia et al.: Timing of microbubble enhanced sonothrombolysis strongly predicts . . . Neruosonology Conference 2008 Genova Italy (abstr).
Molina et al.: Microbubble administration accelerates clot lysis during continuous 2-MHz ultrasound monitoring in stroke patients treated with intravenous tissue plasminogen activator. Stroke 37:425-429, (2006).

(56) References Cited

OTHER PUBLICATIONS

Dorny, "A self-survey technique for self-cohering of antenna systems" Antennas and Propagation, IEEE Transactions on (vol. 26 , Issue: 6 ) pp. 877-881 1978.

Flax et al., "Phase-aberration correction using signals from point reflectors and diffuse scatterers: basic principles" IEEE Trans Ultrason Ferroelectr Freq Control. 1988;35(6):758-67.

Thorn, T., et al., Heart disease and stroke statistics—2006 update: a report from the American Heart Association Statistics Committee and Stroke Statistics Subcommittee. Circulation, 2006. 113(6): p. e85-e151.

Kandzari, D. E., et al., Frequency, Predictors, and Outcomes of Drug-Eluting Stent Utilization in Patients With High-Risk N on-ST-Segment Elevation Acute Coronary Syndromes, the American Journal of Cardiology, 2005. 96(6): p. 750-755.

Rao, S.V., et al., On-Versus Off-Label Use of Drug-Eluting Coronary Stents in Clinical Practice (Report from the American College of Cardiology National Cardiovascular Data Registry [NCDR]). The American Journal of Cardiology, 2006. 97(10): p. 1478-1481.

FDA, Circulatory Systems Devices Advisory Panel, Dec. 7, 2006. Transcript:]rtiygi//w^^ .

Hendrix, J., et al., 5' CArG degeneracy in smooth muscle {alphaj-actin is required for injury-induced gene suppression in vivo. J. Clin. Invest., 2005. 115(2): p. 418-427.

McDonald, O., et al., Control of SRF binding to CArG box chromatin regulates smooth muscle gene expression in vivo. J. Clin. Invest., 2006. 116(1): p. 36-48.

Owens, G., M. Kumar, and B. Wamhoff, Molecular Regulation of Vascular Smooth Muscle Cell Differentiation in Development and Disease. Physiol. Rev., 2004. 84(3): p. 767-801.

Wamhoff, B., et al., L-type Voltage-Gated Ca2+ Channels Modulate Expression of Smooth Muscle Differentiation Marker Genes via a Rho Kinase/Myocardin/SRF-Dependent Mechanism. Circulation Research, 2004. 95(4): p. 406-414.

Braun, M., et al., Cellular adhesion molecules on vascular smooth muscle cells. Cardiovascular Research, 1999. 41(2): p. 395-401.

Braun-Dullaeus, R., et al., Cell cycle-dependent regulation of smooth muscle cell activation. Arterioscler Thromb Vase Biol, 2004. 24: 845-850, 2004: p. 845-850.

Landry, D., et al., Activation of the NF-kappa B and I kappa B system in smooth muscle cells after rat arterial injury. Induction of vascular cell adhesion molecule-1 and monocyte chemoattractant protein-1. Am J Pathol, 1997. 151(4): p. 1085-1095.

Parry, T., et al., Drug-eluting stents: sirolimus and paclitaxel differentially affect cultured cells and injured arteries. Eur J Pharmacol, 2005. 524(1-3): p. 19-29.

Wessely, R., A. Schomig, and A. Kastrati, Sirolimus and Paclitaxel on Polymer-Based Drug-Eluting Stents: Similar But Different. Journal of the American College of Cardiology, 2006. 47(4): p. 708-714.

Webster, A., et al., Target of rapamycin inhibitors (sirolimus and everolimus) for primary immunosuppression of kidney transplant recipients: a systematic review and meta-analysis of randomized trials. Transplantation, 2006. 81(9): p. 1234-1248.

Ross, R., The pathogenesis of atherosclerosis: a perspective for the 1990s. Nature, 1993. 362: p. 801-809.

Denger, T. and T. Pober, Cellular and molecular biology of cardiac transplant rejection. Journal of Nuclear Cardiology, 2000. 7: p. 669-685.

Sheridan, F., P. Cole, and D. Ramage, Leukocyte adhesion to the coronarymicrovasculature during ischemia and reperfusion in an in vivo canine model. Circulation, 1996.93: p. 1784-1787.

Villanueva, F., A. Klibanov, and W. Wagner, Microbubble-endothelial cell interactions as a basis for assessing endothelial function. Echocardiography, 2002. 19: p. 427-438.

Klibanov, A.L., Targeted Delivery of Gas-Filled Microspheres, Contrast Agents for Ultrasound Imaging. Advanced Drug Delivery Reviews, 1999. 37: p. 139-157.

Klibanov, A., et al., Targeted ultrasound contrast agent for molecular imaging of inflammation in high-shear flow. Contrast Media and Molecular Imaging, 2006. 1(6): p. 259-266.

Rosenschein, U., et al., Ultrasound Imaging-Guided Noninvasive Ultrasound Thrombolysis. Circulation, 2000. 102: p. 238-245.

Chan, An image-guided high intensity focused ultrasound device for uterine fibroids treatment. Medical Physics, 2002. 29(11): p. 2611-2620.

Vaezy, S., et al., Ultrasound image-guided therapy. Academic Radiology, 2003. 10(8): p. 956.

Vaezy, S., et al., High intensity focused ultrasound for hemostasis of femoral artery catheter wounds. Ultrasound in Medicine and Biology, 2006. 32(5 Supplement 1): p. 100.

Crum, L., Guided High Intensity Focused Ultrasound (HIFU) for Mission—Critical Care, 2004 p. 1-4.

Bouakaz, A., F. Cate, and N. de Jong, A new ultrasonic transducer for improved contrast nonlinear imaging. Physics in Medicine & Biology, 2004. 49(16): p. 3515-3525.

Forsberg, F., et al., Design and acoustic characterization of a multi-frequency harmonic array for nonlinear contrast imaging. Proceeding of 2001 IEEE Ultrasonics Symposium, 2001.2: p. 1721-1724.

Rychak, J. A. Klibanov, and J. Hossack, Acoustic Radiation Force Enhances Targeted Delivery of Ultrasound Contrast Microbubbles: In vitro Verification. IEEE Transactions on Ultrasonics Ferroelectrics & Frequency Control, 2005. 52(3): p. 421-433.

Marx, S. et al. Rapamycin-FKBP Inhibits Cell Cycle Regulators of Proliferation in Vascular Smooth Muscle Cells. Circulation Research, 1995. 76(3): p. 412-417.

Klibanov, A., et al., Klibanov, A., et al., Attachment ofligands to gas-filled microbubbles via PEG spacer and lipid residues anchored at the interface. Proc. Intl. Symp. Control. Rel. Bioact. Mat., 1999. 26: p. 124-125.

Wilson, T., et al., The ultrasonix 500RP: A commercial ultrasound research interface. IEEE Transactions Ultrasonics, Ferroelectrics and Frequency Control, 2006. 53(10): p. 1772-1782.

Takalkar, A., et al., Binding and detachment dynamics of microbubbles targeted to P-selectin under controlled shear flow. Journal of Controlled Release, 2004. 96(3): p. 473-482.

Klibanov, A., et al., Detection of individual microbubbles of an ultrasound contrast agent: fundamental and pulse inversion imaging. Academic Radiology, 2002: p. S279-S281.

Jayaweera, A., et al., In vivo myocardial kinetics of air-filled albumin microbubbles during myocardial contrast echocardiography. Comparison with radiolabeled red blood cells. Circulation Research, 1994. 74(6): p. 1157-1165.

Springer, T., Adhesion receptors of the immune system. Nature, 1990. 347: p. 425-434.

Dayton, P., et al., Acoustic radiation force in vivo: a mechanism to assist targeting of microbubbles. Ultrasound in Medicine & Biology, 1999. 25(8): p. 1195-1201.

Fowlkes, J., et al., the role of acoustic radiation force in contrast enhancement techniques using bubble-based ultrasound contrast agents. Journal of the Acoustical Society of America, 1993. 93: p. 2348.

Zhao, S., et al., Radiation force assisted targeting facilitates ultrasonic molecular imaging. Molecular Imaging, 2004. 3: p. 1-14.

Shortencarier, J., et al., A method for radiation-force localized drug delivery using gas-filled lipospheres. IEEE Trans. Ultrasonics, Ferroelectrics and Frequency Control, 2004. 51: p. 822-831.

Dayton, P., et al., A preliminary evaluation of the effects of primary and secondary radiation forces on acoustic contrast agents. IEEE Transactions on Ultrasonics Ferroelectrics & Frequency Control, 1997. 44(6): p. 1264-1277.

Dayton, P., J. Allen, and K. Ferrara, The magnitude of radiation force on ultrasound contrast agents. Journal of the Acoustical Society of America, 2002. 112: p. 2183-2192.

Bosse, R. and D. Vestweber, Only simultaneous blocking of the L- and P-selectin completely inhibits neutrophil migration into mouse peritoneum. European Journal of Immunology, 1994. 24: p. 3019-3024.

(56) References Cited

OTHER PUBLICATIONS

Lindner, J., et al., Ultrasound Assessment of Inflammation and Renal Tissue Injury With Microbubbles Targeted to P-Selectin. Circulation, 2001. 104(17): p. 2107-2112.

Burns, P., S. Wilson, and D. Simpson, Pulse inversion imaging of liver blood flow: improved method for characterizing focal masses with microbubble contrast. Invest Radiol, 2000. 35(1): p. 71.

Phillips, P., Contrast Pulse Sequences (CPS): Imaging non-linear microbubbles. Proceedings of the 2001 IEEE Ultrasonics Symposium, 2001.2: p. 1739-1745.

Unger, E., et al., Acoustically active lipospheres containing paclitaxel—A new therapeutic ultrasound contrast agent. Investigative Radiology, 1998. 33: p. 886-892.

Boudennaia, T.Y. and KX. Napoli, Validation of a practical liquid chomatography with ultraviolet detection method for quantification of whole-blood everolimus in a clinical TDM laboratory. Therapeutic Drug Monitoring, 2005. 27(2): p. 171-177.

FDA, Circulatory Systems Devices Advisory Panel, Dec. 8, 2006. Transcript:]rtiygi//w^^.

Klibanov, A., et al., Polymeric sialyl Lewis X microbubbles: targeted ultrasound contrast agents for molecular imaging of inflammation. RSNA Abstract Book, 2006(Abs. # SSK06-06): p. 436-437.

Price, et al., Delivery of Colloidal Particles and Red Blood Cell to Tissue Through Microvessel Ruptures Created by Targeted Microbuble Destruction with Ultrasound. 1998, 98, No. 13, pp. 1264-1267.

Stephens, DN et al. "Multi-frequency Array Development for Drug Delivery Therapies", 2006 IEEE Ultrasonics Symposium.

Reference citations cited in Office Action in EP 08841415.6-1659 dated Nov. 11, 2016.

\* cited by examiner

METHOD AND APPARATUS FOR ACCELERATED DISINTEGRATION OF BLOOD CLOT

CROSS-REFERENCE

This application is a continuation-in-part application of co-pendingapplication Ser. No. 14/063,830, filed on Oct. 25, 2013, which is a continuation application of application Ser. No. 12/739,128, filed on Aug. 9, 2010, now U.S. Pat. No. 8,622,911, issued on Jan. 7, 2014. Application Ser. No. 12/739,128 is an application that was filed under 35 U.S.C. 371 claiming priority to International Application PCT/US2008/081189, filed Oct. 24, 2008, which claims priority to U.S. Provisional Application Ser. No. 61/000,632, filed Oct. 26, 2007, entitled "Molecular Targeted Microbubbles for Enhanced Blood Vessel Imaging and Therapeutic Treatment of Neointimal Hyperplasia;" and U.S. Provisional Application Ser. No. 61/099,025, filed Sep. 22, 2008, entitled "Molecular Targeted Microbubbles for Enhanced Blood Vessel Imaging and Therapeutic Treatment of Neointimal Hyperplasia". Each of the aforementioned applications and patent is hereby incorporated herein, in its entirety, by reference thereto, and we claim priority to each of the aforementioned applications.

GOVERNMENT RIGHTS

This invention was made with government support under Federal Grant No. HL090700 and Federal Grant No. 5R01EB002185-7, awarded by The National Institutes of Health. The Government has certain rights in the invention.

FIELD OF THE INVENTION

The present invention relates to apparatus, systems and methods for dissolving blood clots. In one particular aspect the present invention relates to dissolution of blood clots in the brain.

BACKGROUND OF THE INVENTION

Stroke is the third leading cause of death (after heart disease and cancer) and the leading cause of disability, as reported by Ingall: Stroke-incidence, mortality, morbidity and risk. J Insur Med 36(2):143-152 (2004). The annual total economic cost of stroke is estimated at $68.9 billion, as of 2004. There are 795,000 strokes annually in the United State of America, according to Lloyd-Jones et al.: Heart disease and stroke statistics—2009 update. Circulation 119(3):480-486 (2009). First strokes account for 75% of these strokes and 18% of stroke victims die from their stroke. Death resultant from stroke is greater among women (61% women, 39% men). The World Health Organization estimates that there are 15 million strokes annually worldwide and approximately 5 million of these stroke victims die and another 5 million are permanently disabled.

Problem to be Solved

The current standard of care for stroke patients is admittance to the Emergency Room or other emergency treatment facility followed immediately by a computed tomography (CT) scan to determine whether the stroke is ischemic (blockage) or hemorrhagic (ruptured) and to assess the location and extent of ischemia in the brain. If the patient is admitted soon enough after the onset of ischemic stroke (<3 hours generally, <4.5 hours in some cases), then tissue Plasminogen Activator (tPA) is administered. Beyond this time "window" (i.e., 3 to 4.5 hours), the FDA does not approve tPA administration due to the risk of hemorrhagic damage to the brain. Unfortunately, tPA administration in patients with ischemic stroke results in only a 30% greater chance of little, or no disability, compared with no tPA at 3 months, as reported by Marler: Tissue plasminogen activator for acute ischemic stroke. N Engl J Med. 333:1581-1587 (1995). Additionally, intracerebral hemorrhage occurs at a 6.4% incidence rate among patients receiving tPA therapy.

The narrow therapeutic time-window and complications associated with tPA administration have driven the development of other approaches for managing ischemic stroke. Beyond 3 or 4.5 hours, and up to 8 hours, mechanical thrombectomy is performed to recannulate the occluded (blocked) blood vessel, but recent trials failed to demonstrate a clinical benefit from the first generation of mechanical devices, see Smith et al., Safety and efficacy of mechanical embolectomy in acute ischemic stroke: results of the MERCI trial. Stroke. 2005 July; 36(7):1432-8. Epub 2005 Jun. 16.(2005). In comparison, the addition of adjuvant ultrasound (with or without microbubbles) has been shown in multiple studies to improve tPA efficacy, as reported by 5. Alexandrov et al: CLOTBUST Investigators: Ultrasound-enhanced systemic thrombolysis for acute ischemic stroke. N Engl J Med 351:2170-2178, (2004); Alexandrov et al.: A pilot randomized clinical safety study of sonothrombolysis. Stroke 39:1464-1469, (2008); Dinia et al.: Timing of microbubble enhanced sonothrombolysis strongly predicts . . . . Stroke 39:559, (2008) (abstr); and Molina et al.: Microbubble administration accelerates clot lysis during continuous 2-MHz ultrasound monitoring in stroke patients treated with intravenous tissue plasminogen activator. Stroke 37:425-429, (2006).

In a recent clinical trial, ischemic stroke patients that were treated with tPA, transcranial ultrasound, and microbubbles had significantly higher rates of recanalization and greater clinical improvement compared with patients who received tPA alone (54.9% versus 31.1%, n=128), see Dinia et al., cited above. Although this represents a significant improvement, tPA administration was still linked to intracerebral hemorrhage, and the combined tPA/US/MB therapy was ineffective in over 30% of patients. Thus, there is a clear need to develop technologies that further enhance tPA efficacy at lower doses and reduce the incidence of intracerebral hemorrhage. Even small improvements in patient outcomes will be impactful based on the large scale of the clinical problem.

SUMMARY OF THE INVENTION

In one aspect of the present invention, a method of treating a blood clot in a patient is provided including: delivering a thrombolytic agent toward the blood clot; and applying ultrasonic energy to the microbubbles to vibrate the microbubbles.

In at least one embodiment, at least 50 percent of the microbubbles dissolve within 120 seconds after production of the microbubbles.

In at least one embodiment, at least 80 percent of a total volume of the microbubbles vanishes after 120 seconds after production of the microbubbles.

In at least one embodiment, at least 50 percent of a total volume of the microbubbles vanishes after 120 seconds after production of the microbubbles.

In at least one embodiment, at least 30 percent of a total volume of the microbubbles vanishes after 120 seconds after production of the microbubbles.

In at least one embodiment, at least 90 percent of the microbubbles dissolve within 120 seconds after production of the microbubbles.

In at least one embodiment, at least 80 percent of the microbubbles dissolve within a time period in the range of from about 30 seconds to about 180 seconds after production of the microbubbles.

In at least one embodiment, at least 80 percent of the microbubbles dissolve within 120 seconds after production of the microbubbles.

In at least one embodiment, at least 30 percent of the microbubbles dissolve within 120 seconds after production of the microbubbles.

In at least one embodiment, at least 50 percent of the microbubbles dissolve within a predetermined time period after production of the microbubbles, wherein the predetermined time period is in the range of 30 seconds to 180 seconds.

In at least one embodiment, all of the microbubbles dissolve within ninety seconds after production of the microbubbles.

In at least one embodiment, the microbubbles have an average diameter greater than or equal to about eight micrometers.

In at least one embodiment, the microbubbles have an average diameter greater than or equal to about twenty-five micrometers.

In at least one embodiment, the average diameter is in the range of twenty-five to thirty-five micrometers.

In at least one embodiment, the microbubbles have an average diameter in the range of about eight micrometers to about twenty-five micrometers.

In at least one embodiment, the microbubbles have an average diameter in the range of about ten micrometers to about twenty micrometers.

In at least one embodiment, the microbubbles have an average diameter in the range of about eight micrometers to about twenty-five micrometers.

In at least one embodiment, the microbubbles each have a shell comprising albumin and a core comprising nitrogen.

In at least one embodiment, the microbubbles each have a shell and a core, wherein the core comprises an unstable gas.

In at least one embodiment, the core further comprises a stable gas.

In at least one embodiment, the core comprises a neuroprotective gas.

In at least one embodiment, the blood clot is in the brain of the patient and the ultrasound energy is delivered transcranially.

In at least one embodiment, the blood clot is in a cerebral artery and the catheter is inserted into the cerebral artery.

In at least one embodiment, the blood clot is in a blood vessel, having caused an ischemic stroke.

In at least one embodiment, the blood clot comprises congealed blood resulting from a hemorrhage.

In at least one embodiment, the blood clot is in a vein, having caused deep vein thrombosis.

In at least one embodiment, the blood clot is in a pulmonary artery, having caused a pulmonary embolism.

In at least one embodiment, the thrombolytic agent is delivered intravenously.

In at least one embodiment, the delivery of the thrombolytic agent comprises introducing the thrombolytic agent into a carotid artery of the patient.

In at least one embodiment, the delivery of the thrombolytic agent comprises delivering the thrombolytic agent from a distal end portion of the catheter.

In at least one embodiment, the microbubbles are produced by a microfluidics device.

In at least one embodiment, the microfluidics device is provided in the catheter, and inserted into the patient along with the catheter.

In at least one embodiment, the thrombolytic agent comprises tissue Plasminogen Activator (tPA).

In at least one embodiment, the blood clot is in the brain of the patient and the ultrasound energy is delivered from the catheter.

In at least one embodiment, the ultrasound energy is delivered from a location outside the body of the patient to a location inside the patient at or near a location of the blood clot.

In at least one embodiment, the ultrasound energy is delivered from the catheter.

In at least one embodiment, the method further includes real-time monitoring at least one of production rate and size of microbubbles produced.

In at least one embodiment, the real-time monitoring is performed in an automatic feedback loop, the method further comprising automatically adjusting at least one of gas pressure, gas flow rate, liquid pressure and liquid flow rate to maintain stable production rate and size of the microbubbles.

In at least one embodiment, the method further includes concurrent or adjacent use of a thrombectomy device to assist in at least one of breaking up and removing the blood clot.

In at least one embodiment, delivering low stability microbubbles and applying ultrasonic energy comprise: initially delivering a microdose of the microbubbles; receiving ultrasound echo signals from one or more isolated microbubbles; calculating aberrating delays based upon the ultrasound echo signals received from the one or more isolated microbubbles; and superimposing the aberrating delays on at least one of transmit and receive phases of the ultrasound energy.

In at least one embodiment, the method further includes: incrementally increasing power of the transmit ultrasound energy to determine a threshold power level where microbubble destruction, such as by cavitation or other form of destruction is observed to start occurring; reducing the power of the transmit ultrasound energy to a reduced power level comprising a predetermined percentage of the threshold power level; and delivering the microbubbles at full dose and applying the ultrasound energy to the microbubbles at the reduced power level.

In at least one embodiment, a frequency of the transmit ultrasound energy is matched to a resonance frequency of the microbubbles.

In at least one embodiment, a frequency of the transmit ultrasound energy is off-resonance relative to a resonance frequency of the microbubbles.

In at least one embodiment, the method is carried out and monitored using ultrasound imaging, without any use of fluoroscopy or X-ray imaging.

In at least one embodiment, the low stability microbubbles are outputted from a microfluidics device in the catheter, the microfluidics device comprising an outlet port from which the low stability microbubbles are outputted, and wherein a distance from the outlet port to the clot is 5 cm or less.

In at least one embodiment, the distance is in the range of 2 cm to 4 cm.

In another aspect of the present invention, a system for treating a blood clot is provided, including: a catheter configured to be inserted into a patient; low stability microbubbles; the catheter configured to deliver the microbubbles toward the blood clot in the patient; and an ultrasonic energy device configured to apply ultrasonic energy to the microbubbles to vibrate the microbubbles.

In at least one embodiment, at least fifty percent of the microbubbles dissolve within one hundred twenty seconds after production of the microbubbles.

In at least one embodiment, all of the microbubbles dissolve within ninety seconds after production of the microbubbles.

In at least one embodiment, the microbubbles have an average diameter greater than or equal to about eight micrometers.

In at least one embodiment, the microbubbles have an average diameter greater than or equal to about twenty-five micrometers.

In at least one embodiment, the average diameter is in the range of twenty-five to thirty five micrometers.

In at least one embodiment, the microbubbles have an average diameter in the range of about eight micrometers to about twenty-five micrometers.

In at least one embodiment, the microbubbles have an average diameter in the range of about ten micrometers to about twenty micrometers.

In at least one embodiment, the microbubbles have an average diameter in the range of about eight micrometers to about twenty-five micrometers.

In at least one embodiment, the microbubbles are polydisperse, with a minimum diameter of about one micrometer and a maximum diameter of about one hundred micrometers.

In at least one embodiment, the microbubbles each have a shell comprising albumin and a core comprising nitrogen.

In at least one embodiment, the microbubbles each have a shell and a core, wherein the core comprises an unstable gas.

In at least one embodiment, the core further comprises a stable gas.

In at least one embodiment, the core further comprises a neuroprotective gas.

In at least one embodiment, the core comprises an unstable gas and a neuroprotective gas.

In at least one embodiment, the core comprises an unstable gas a stable gas and a neuroprotective gas.

In at least one embodiment, the blood clot is in the brain of the patient and the ultrasound energy device is configured to apply ultrasound energy from outside the patient's body, trans-cranially to the microbubbles.

In at least one embodiment, the blood clot is in a cerebral artery and the catheter is configured and dimensioned to be inserted into the cerebral artery.

In at least one embodiment, the blood clot is in a femoral vein and the catheter is configured and dimensioned to be inserted into the femoral vein.

In at least one embodiment, the blood clot is in an iliofemoral vein and the catheter is configured and dimensioned to be inserted into the iliofemoral vein.

In at least one embodiment, the blood clot is in a popliteal vein and the catheter is configured and dimensioned to be inserted into the popliteal vein.

In at least one embodiment, the blood clot is in an iliac vein and the catheter is configured and dimensioned to be inserted into the iliac vein.

In at least one embodiment, the blood clot is in an inferior vena cava and the catheter is configured and dimensioned to be inserted into the inferior vena cava.

In at least one embodiment, the blood clot is in an axillary vein and the catheter is configured and dimensioned to be inserted into the axillary vein.

In at least one embodiment, the blood clot is in a subclavian vein and the catheter is configured and dimensioned to be inserted into the subclavian vein.

In at least one embodiment, the blood clot is in the microvasculature, having caused microvascular obstruction (MVO) and the catheter is configured and dimensioned to be inserted into an artery that feeds the microvasculature having been obstructed.

In at least one embodiment, the system further includes a delivery tube configured to delivering a thrombolytic agent toward the blood clot.

In at least one embodiment, the system further includes a thrombolytic agent to be applied to the blood clot.

In at least one embodiment, the catheter comprises a delivery channel configured to deliver a thrombolytic agent from a distal end portion of the catheter toward the blood clot.

In at least one embodiment, the system further includes the thrombolytic agent in the delivery channel.

In at least one embodiment, the catheter includes a microfluidics flow-focusing device contained within the catheter and configured to produce the low stability microbubbles.

In at least one embodiment, the microfluidics flow-focusing device is flexible and capable of being deformed for insertion into the catheter.

In at least one embodiment, the microfluidics flow-focusing device comprises a lamination of polymer layers and can be rolled up to be received within a cylindrical void of the catheter.

In at least one embodiment, the microfluidics flow-focusing device is rigid and comprises glass.

In at least one embodiment, the microfluidics flow-focusing device comprises electrodes configured to operate as a micro Coulter device to measure changes in impedance as the low stability microbubbles flow past the electrodes.

In at least one embodiment, the microfluidics flow-focusing device comprises at least one liquid input channel, a gas input channel, and electrodes positioned in the gas input channel and at least one of the at least one liquid input channel, the electrodes being configured to detect electrical conductivity.

In at least one embodiment, the catheter further comprises a microfluidics flow-focusing device configured to produce the low stability microbubbles.

In at least one embodiment, the catheter comprises a microfluidics T-junction device configured to produce the low stability microbubbles.

In at least one embodiment, the catheter comprises a microfluidics co-flow device configured to produce the low-stability microbubbles.

In at least one embodiment, the ultrasonic energy device comprises a transducer contained within the catheter.

In at least one embodiment, the blood clot is in the brain of the patient and the catheter and transducer are configured and dimensioned to be inserted into a blood vessel in the brain.

In at least one embodiment, the blood vessel is a cerebral artery.

In at least one embodiment, the system further includes a tube in fluid communication with and extending distally from a distal tip of the catheter; wherein the catheter has a first outside diameter and the tube has a second outside diameter, the second outside diameter being less than the first outside diameter; and wherein the tube is configured and dimensioned to deliver the microbubbles distally of the catheter.

In at least one embodiment, the tube is configured and dimensioned to deliver the microbubbles into a vessel that is too small for the catheter to be inserted into.

In at least one embodiment, the system further includes at least one sensor configured for real-time monitoring at least one of production rate and size of microbubbles produced.

In at least one embodiment, the microfluidics device further comprises at least one sensor configured for real-time monitoring at least one of production rate and size of microbubbles produced.

In at least one embodiment, the at least one sensor comprises multiple non-polarizing electrodes.

In at least one embodiment, the at least one sensor comprises multiple optical waveguides.

In at least one embodiment, the real-time monitoring is performed in an automatic feedback loop, the system further comprising an automatic control system configured to automatically adjust at least one of gas pressure and liquid flow rate to maintain stable production rate and size of the microbubbles.

In at least one embodiment, the real-time monitoring is performed in an automatic feedback loop, the system further comprising an automatic control system configured to automatically adjust at least one of gas pressure and liquid flow rate to temporarily stop microbubble production or to resume microbubble production from an off state.

In at least one embodiment, the system further includes a thrombectomy device to assist in breaking up the blood clot.

In at least one embodiment, the transducer comprises one or more transducers configured for ultrasonic imaging as well as for the applying ultrasonic energy to vibrate the microbubbles.

In another aspect of the present invention, a method of treating a blood clot is provided, including: inserting a catheter into a patient; delivering low stability microbubbles toward the blood clot in the patient; measuring the diameters of the low stability microbubbles in real time; and changing the diameters of microbubbles produced by varying at least one of gas pressure and liquid flow rate input to a microfluidics device the produces the microbubbles.

In at least one embodiment, the microfluidics device comprises electrodes configured to operate as a micro Coulter device to measure changes in impedance as the microbubbles flow past the electrodes.

In at least one embodiment, the microfluidics device comprises optical waveguides configured to operate as a micro particle sizer to measure changes in optical transmission and reflections as microbubbles flow past the waveguides.

In at least one embodiment, the method further includes changing at least one of: liquid composition or gas composition to alter a half-life of the low stability microbubbles produced.

In another aspect of the present invention, a system for treating a blood clot is provided, including: a catheter configured to be inserted into a patient; and a microfluidics device contained in a distal end portion of the catheter, the microfluidics device configured to produce low stability microbubbles, the microfluidics device comprising electrodes configured to operate as a micro Coulter device to measure changes in impedance as the low stability microbubbles flow past the electrodes.

In at least one embodiment, the microfluidics device is configured to produce the low stability microbubbles having a diameter in the range of 10 μm to 35 μm.

In at least one embodiment, the microfluidics device comprises an outlet port from which the microbubbles are outputted, the catheter comprising a distal end; and wherein the outlet port is positioned at a distance in the range of from 0 mm to 3 mm from the distal end.

In at least one embodiment, the distance is in the range of from 0.5 mm to 1 mm.

In at least one embodiment, the distance is about 1 mm.

In at least one embodiment, the outlet port is positioned at a distance from the clot in the range of from about 0 mm to 5 cm.

In at least one embodiment, the outlet port is positioned at a distance from the clot in the range of from about 0 mm to 10 mm.

These and other advantages and features of the invention will become apparent to those persons skilled in the art upon reading the details of the invention as more fully described below.

DETAILED DESCRIPTION OF THE INVENTION

Figure 1:
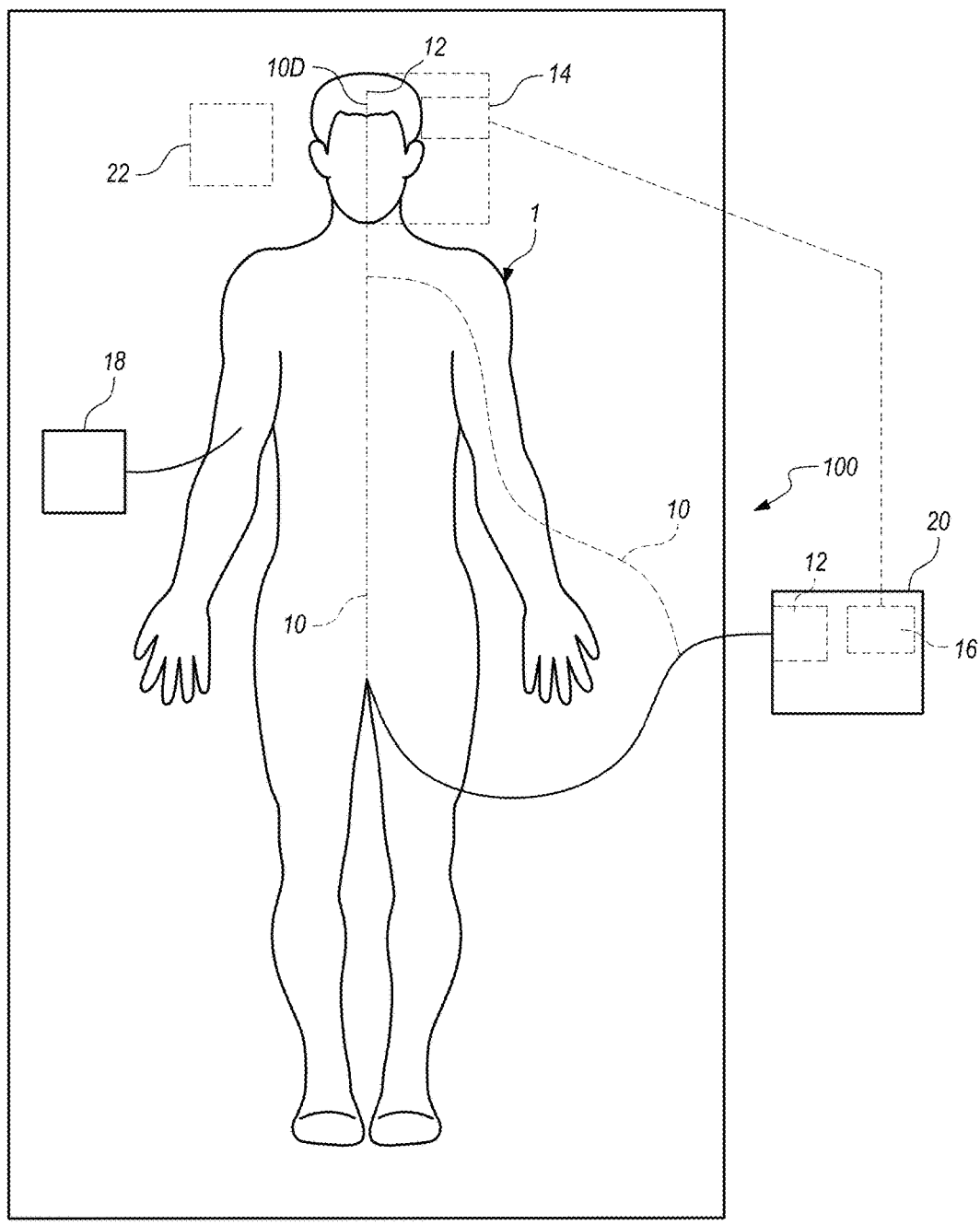
FIG. 1 is a schematic illustration of apparatus being used to facilitate lysis of a blood clot in a cerebral artery in the brain of a patient, according to an embodiment of the present invention.

Before the present methods and apparatus are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference, in their entireties, to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a microbubble" includes a plurality of such microbubbles and reference to "the electrode" includes reference to one or more electrodes and equivalents thereof known to those skilled in the art, and so forth.

The publications discussed herein are provided solely for their disclosure prior to the filing date of the present application. The dates of publication provided may be different from the actual publication dates which may need to be independently confirmed.

Definitions

"Erosion" as used herein, refers to the rate of removal of clot volume, expressed either in percentage per time or volume per time.

"Dissolution" as used herein refers to the gas inside a microbubble being lost through the microbubble shell or membrane.

"Low stability" as used herein, refers to having lifetime (measured by half-life, for example) being less than three minutes, possibly as little as 5-10 seconds. Examples of low stability microbubbles include those formed with an unstable shell formulation (i.e. contrary to the common goal of currently known microbubble design) and unstable gas (e.g., a gas chosen for its rapid rate of diffusion out of the shell and into the blood plasma). Examples of unstable gases include, but are not limited to: $O_2$, $N_2$, $CO_2$, or blends thereof, with or without a portion of a stable gas such as $C_4F_{10}$ or $C_3F_8$ or $SF_6$.

An "unstable gas", as used herein, refers to a gas with a solubility in water that is higher than 10 mg gas per 1 L of water at 25 C. High solubility gases diffuse into water quickly and yield a microbubble with short lifetimes, i.e. an "unstable microbubble". Examples of unstable gases include, but are not limited to: $O_2$, $N_2$ and $CO_2$.

An "unstable shell formulation" or "unstable shell", as used herein, refers to a shell formulation that forms a shell or coating at the liquid/gas interface of the microbubble that provides a weak barrier to gas diffusion out of the microbubble and into the aqueous medium. An unstable shell formulation includes one or more of the following characteristics: (1) a protein-based surfactant that is not cross-linked; (2) a lipid-based surfactant used above the melt temperature (Tm) of the lipid; (3) a lipid-based surfactant that is comprised of lipids with a single hydrophobic tail; and/or (4) a lipid-based surfactant with no pegylation.

A "stable gas", as used herein, refers to a gas with a solubility in water that is less than 10 mg gas per 1 L of water at 25 C. Examples of stable gases, include, but are not limited to: $C_4F_{10}$ and $SF_6$.

A "stable shell formulation" or "stable shell", as used herein, refers to one or more of the following: (1) a protein-based shell material that is cross-linked; (2) a lipid-based shell material that is below its lipid melt temperature (Tm); (3) a lipid-based shell material that is comprised of lipids with two hydrophobic tails; and/or (4) a shell material that has been pegylated.

A "neuroprotective gas" as used herein, refers to one or more of a set of gases that confer neuroprotection during ischemic stroke events and reduce tissue loss due to ischemia. Examples of neuroprotective gases include, but are not limited to: hydrogen (H2), nitrous oxide (N2O), xenon, isofluorane, sevofluorane, halothane, nitric oxide (NO), or blends thereof.

The term blood clot refers to a gelatinous or semisolid mass of coagulated blood, including, but not limited to those that form a complete or partial blockage of a blood vessel, such as those blood clots that cause ischemic stroke, heart attack, etc. A "blood clot" may refer to congealed blood, for example, as occurs in hemorrhagic stroke or other cause of blood leaking from a vessel, pooling and congealing. The present invention can facilitate liquifying of the congealed blood to facility its extraction.

DETAILED DESCRIPTION

A purpose of the present invention is to extend the efficacious and safe window for clinical use of tPA-based therapy or other thrombolytic agent-based therapy. Microbubble fabrication techniques are used to design and provide novel microbubbles with properties specifically tailored to further enhance the adjuvant provided will permit the use of a lower dosage of thrombolytic agent compared to that applied in current techniques and thereby implicitly reduce risk of hemorrhage and/or extend the time window for safe tPA-based (or other thrombolytic agent-based) therapy. Consequently, the number of patients safely and successfully treated may be significantly increased.

FIG. 1 is a schematic illustration of apparatus 100 being used to facilitate lysis of a blood clot in a cerebral artery in the brain of a patient 1. It is noted here that the apparatus and methods of the present invention are not limited to treatment of blockages/blood clots in the cerebral arteries, but are applicable to other arteries in the brain, including arteries downstream of the cerebral arteries. Additionally, the present apparatus and methods can be applied to blood clots and other blockages in other locations in the body such as, but not limited to: deep vein thrombosis (DVT), pulmonary embolism, etc.

Apparatus 100 includes a minimally-invasive intravascular device that applies a stream of microbubbles 30 to a target location within a vessel of the patient adjacent to a blockage/blood clot. In the embodiment shown in FIG. 1, a catheter 10 is configured and dimensioned to be minimally-invasively inserted into patient 1. In the embodiment shown, catheter 10 is inserted into the femoral artery (or optionally, alternatively, into the radial artery or other artery) of the patient 1 and advanced so that the distal tip portion 10D is located in a target cerebral artery adjacent (slightly upstream) of the location of a blockage in the cerebral artery. Vascular access into the cerebral arteries requires that the outside diameter of the catheter 10 be no more than about 2 mm in diameter (6 F).

A microbubble source 12 is provided in catheter 10 (preferably, but not necessarily limited to the distal end portion or distal tip of the catheter 10) to supply a stream of microbubbles that are delivered out of the distal end portion of the catheter 10 toward the blockage. Alternatively, microbubble source can be located at or in hydraulic communication with a proximal end portion of the catheter 10.

An ultrasound source (transducer or transducer array) 14 is provided in the embodiment of FIG. 1 to administer low frequency ultrasound waves trans-cranially to the surgical target area. Alternatively, the ultrasound source can be provided in the distal end portion of the catheter, not shown in FIG. 1, but described in more detail below. In at least one embodiment using the external (of the patient's body) ultrasound source 14, a Philips P4-2 transducer array (Philips Healthcare, Andover, Mass.) is used. A Verasonics research scanner 16 (V1 or Vantage systems from Verasonics, Bothell, Wash.) is provided in an external controller 20 and paired with the ultrasound source 14. Scanner 16 is programmable and can be used to switch between anatomic and Color Doppler imaging modes and a therapeutic delivery mode.

An optimal therapeutic mode in one embodiment includes a 500 kHz center frequency, a 500 kPa peak negative pressure, with an on period of 1-5 s and an off period of 1-10 s, corresponding to a total duty cycle of approximately 30%. However, each of frequency, pressure and 'on'/'off' times may vary. For example, frequency may range from 100 kHz to 10 MHz (although most in the 1 MHz region), peak pressure may vary from 100 kPa to 1 MPa and the on/off periods may vary extensively (e.g., 0.1-20 s with many permutations of on/off ratio). Anatomic (B-Mode) imaging is used to observe the anatomy in question. B-Mode provides cross-sectional information and assists with placing the therapeutic focus centered upon the intended target zone. Typically, the therapeutic zone will lie central in the imaging plane at some depth. When using an array-based system, the therapeutic focus can be user selected. In a simpler system, the therapeutic source may be a fixed focal depth single element transducer. Thus, the user can manipulate the imaging plane until the focal zone of the therapeutic transducer is located right over the intended anatomy—e.g. the blood clot in a blood vessel.

Doppler modes—especially Color Doppler—can be used to observe or sense the presence of blood flow. For example, during the process of opening a blood vessel previously occluded by clot, the increasing presence of blood flow indicates a positive therapeutic result. Other Doppler modes are possible—e.g. audible (PW) Doppler gives an audible indication of blood flow. Doppler, in various modes, gives an indication of velocity of flow and volume (or area) of flow. Both of these have value in guiding the procedure. PW Doppler (audible or video) provides an indication of peak blood velocity and also the approximate volumetric flow character of the blood. As blood flow is recovered as the procedure is successful in removing a clot, it is anticipated that small high velocity blood "jets" may be replaced by a wider cross-section of blood that may move a more uniform velocity. Notice that a "jet" may or may not occur in the case of a partial occlusion depending on the degree of restriction and any downstream resistance to flow. In any event, changes in blood flow quality (velocity or cross-sectional area of flowing blood) are of diagnostic and therapy guidance value. Color Doppler is usually implemented as an extension of PW Doppler. In effect PW Doppler signals are acquired across a range of lateral and depth locations according to a user selected "Color Box" that defines the region of interest to be interrogated. Peak or average velocity values are color coded and displayed. i.e. various shades of red and blue denote varying velocities of blood flowing towards or away from the transducer. Color Doppler is, by nature, more graphical than PW Doppler used to produce an audible or a velocity time varying "strip" (i.e. a moving strip showing the variance of various PW Doppler detected velocities as a function of time—typically called PW Spectral Doppler)

At the same time (or slightly prior to or slightly after) microbubbles are being streamed to the blockage and ultrasound is directed to the blockage, a thrombolytic agent is systemically introduced and delivered to the blockage in the location of surgical target area. In the embodiment shown in FIG. 1, a thrombolytic agent source 18 delivers the thrombolytic agent intravenously into the patient 1 and the thrombolytic agent used is tissue plasminogen activator (t-PA). However, other thrombolytic agents may be used additionally or alternatively to t-PA, including one or more of abciximab, rt-PA (alteplase), anisoylated plasminogen streptokinase activator complex (APSAC), TNK-rt-PA (tenecteplase), reteplase, monteplase, lanoplase, pamiteplase, staphylokinase, abciximab, tirofiban, orbofiban, xemilofiban, sibrafiban, urokinase (Kinlytic) and/or roxifiban.

Alternatively, the thrombolytic agent may be administered more locally, such as through the carotid artery, or still more locally, from the distal end portion of catheter 10. This further reduces the dosage required to be applied for efficacy and further reduces the risk of intracerebral hemorrhage. The highly localized nature of thrombolytic agent delivery from catheter 10 may enable the use of one or more thrombolytic agents that have previously failed in drug trials for treatment of blockages due to side effect risks of hemorrhage when applied systemically in doses necessarily larger than those required when delivered in a highly localized manner as described.

In the embodiment of FIG. 1, catheter 10 is inserted into the patient as described above, under visual guidance using X-ray fluoroscopy provided by fluoroscope 22, for example. In an alternative embodiment, the distal end portion of catheter 10 can be provided with side and/or forward looking ultrasound imaging capabilities so that catheter 10 can be inserted and placed without the need for fluoroscopy. Examples of catheters with distal end portions provided with side and/or forward looking ultrasound imaging capabilities can be found in U.S. application Ser. No. 12/739,128, now U.S. Pat. No. 8,622,911. Once the distal tip 10D is placed adjacently upstream of the blockage as desired, controller 20 can be operated to activate the apparatus 100 to deliver microbubbles to the blockage and thrombolytic agent is also applied to the blockage, either by the systemic introduction or a more localized application, as described. Ultrasound waves are applied trans-cranially (in the embodiment of FIG. 1, or, alternatively, from catheter 10) to the target location (location of the clot and adjacent microbubbles).

Using a trans-cranial, Doppler compatible, transducer and programmable scanner allows for interleaving drug delivery with anatomic and Color Doppler imaging so as to observe increasing blood flow resulting from a successful clot dissolution exercise. Consistent with previous uses of trans-cranial ultrasound for sonothrombolysis, the trans-cranial transducer may be held in a position via a head-frame positioned rigidly with respect to the head surface. Significantly, the approaches described herein enable real-time, non-invasive, radiation-free, guidance of the procedure.

The application of ultrasound agitates and/or mixes the microbubbles and thrombolytic agent and facilitates more active transport of the thrombolytic agent into the clot. The microbubbles are typically not designed to be burst by the application of ultrasound, but in the event that one or more microbubbles does burst under application of ultrasound, this may further contribute to lysis of the clot. "Anatomic" mode ultrasound is used to provide conventional ultrasound imaging of structure. No information about organ function (e.g., blood flow, etc.) is provided by anatomic mode, but a geometric map of the underlying tissue structure is provided. "Color Doppler" mode ultrasound is used to image the blood flow to show its increase as the blood clot is lysed. Also, this imaging of the flow shows where the blood clot is lysed. Further, Color Doppler mode pulses may provide some therapeutic effect. "Radiation force" ultrasound can optionally be used, as described in U.S. Pat. No. 8,622,911. However, a preferred embodiment relies on residual blood flow to carry microbubbles and drug to the clot. As the clot is lysed by application of thrombolytic agent, microbubbles and, optionally, ultrasound energy, thereto, increase of blood flow past the location of the clot can be monitored visually using the Color Doppler mode of ultrasound. Once the lysis of the blood clot has been completed, ultrasound application is discontinued and application of microbubbles is discontinued. Application of thrombolytic agent may be discontinued at this time if it has not already been discontinued (which is more typically the case) after a predetermined dosage has been applied. Catheter 10 can then be removed from the patient and the entrance opening(s) for the catheter 10 (and introduction of thrombolytic agent, when it is applied separately) is/are closed to complete the procedure.

Figure 4:
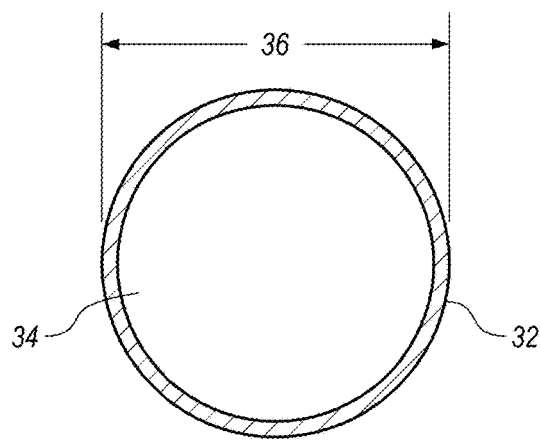
FIG. 4 is a schematic, cross-sectional illustration of a microbubble according to an embodiment of the present invention.

Microbubbles can be produced by a flow-focusing microfluidic device 12' incorporated into the distal tip of the catheter 10. Flow-focusing microfluidic devices contain micro-channels that direct the flow of gas and liquid towards a nozzle to produce micrometer sized microbubbles 30. This microbubble fabrication approach enables the production of microbubbles with diameters 36 (see FIG. 4) ranging between about 8 and 25 micrometers at production rates up to 1,000,000 microbubbles per second.

Figure 2:
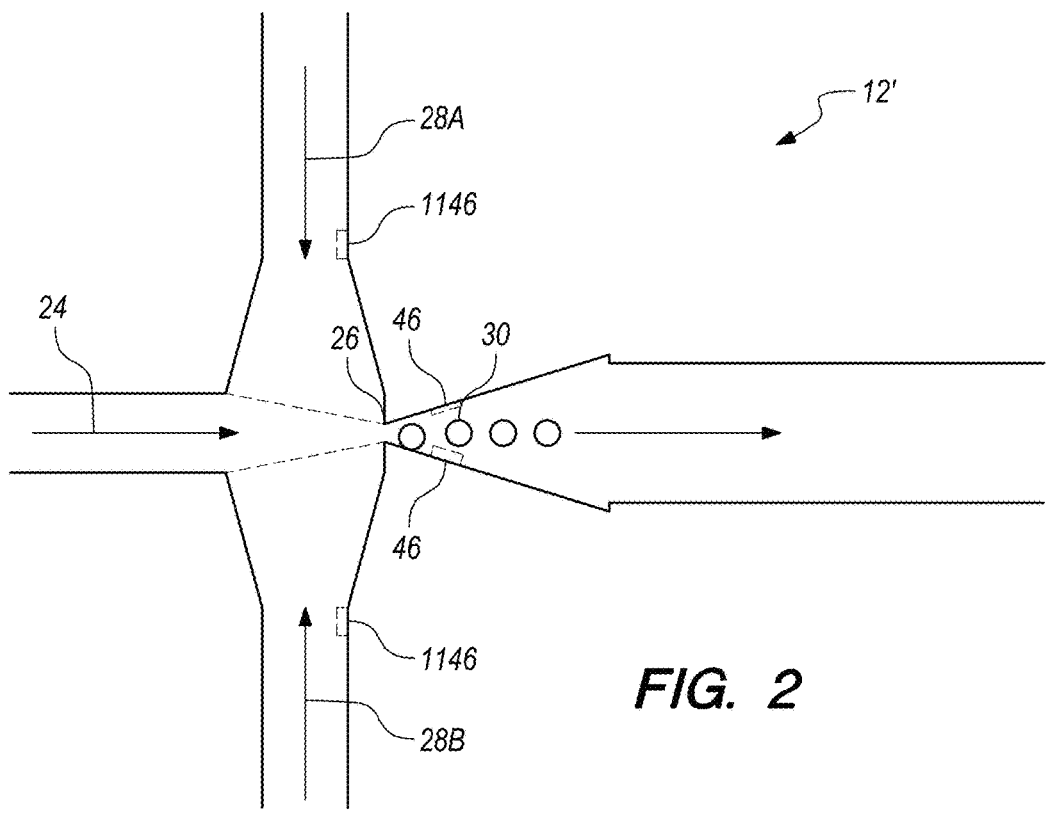
FIG. 2 illustrates a schematic plan view of a microfluidic device that can be used as microbubble source, according to an embodiment of the present invention.

FIG. 2 illustrates a schematic plan view of a microfluidic device 12' that can be used as microbubble source 12 when the microbubble source 12 is provided in catheter 10. A gas stream 24 (e.g., nitrogen, air, or other gas) is focused at a nozzle 26 by two liquid streams 28A, 28B to produce microbubbles 30 that are emitted from nozzle 26. The liquid in the liquid streams 28A,28B forms the shells 32 (see FIG. 4) of the microbubbles 30, the cores 34 of which are filled with the gas from the gas stream 24. In at least one embodiment, the shells comprise blood-derived albumin and the gas inside the shells comprises nitrogen or air. However, microbubbles could be produced from alternative liquids (shells) and/or gases. For example, alternative gases include, but are not limited to: oxygen, nitrogen, carbon dioxide and mixtures thereof. Optionally, one or more neuroprotective gases, including, but not limited to: hydrogen, nitrous oxide, xenon, isofluorane, and/or sevofluorane may be added to the mixture. Diffusion of these gases out of the microbubbles in the vicinity of the clot is believed to confer neuroprotective effects and reduce the rate of ischemic tissue loss. Optionally, one or more of more stable gases, including, but not limited to: perfluorobutane, perfluoropropane, and/or sulphur hexafluoride may be added to the mixture. Among the "unstable" gases ("unstable" is used not to describe the gas being unstable in the chemical sense, but in its characteristic to more rapidly diffuse past the shell membrane of the microbubble, out into the blood plasma, as compared to the more "stable" gases mentioned above), $CO_2$ is believed to contribute towards the shortest bubble lifetime (referred to herein as "half-life" to describe a measure of the stability of a population of microbubbles). It is further noted that a blend of stable gas (e.g., $C_4F_{10}$, or the like) and unstable gas (e.g., $CO_2$ or the like results in a rapid dissolution of the unstable gas out of the microbubble, with a much slower dissolution of the stable gas out of the microbubble. For example, a microbubble filled with 75% $CO_2$ and 25% $C_4F_{10}$ (both volume percentages), results in the microbubble rapidly shrinking to 25% of original volume after the $CO_2$ dissolves rapidly out of the microbubble, followed by a much slower dissolution of the $C_4F_{10}$ out of the microbubble stable gas. Examples of materials that can be used to form the shell of the microbubble include, but are not limited to: albumin, propylene glycol (PG), polyethylene glycol (PEG), sucrose, dextrose, glycerol, PEG40-stearate, fluorosurfactant, etc.

This approach has many features and characteristics: (1) increased versatility, as the composition and size can be varied "on the fly"; and (2) enables otherwise unfeasible microbubbles. Making the microbubbles at the distal tip portion 10D mitigates stability problems, as the microbubbles only have to survive a few seconds before therapeutic delivery. This may enable focal delivery of neuroprotective gases that otherwise cannot be encapsulated within conventional microbubble formulations. Further, this may enable less stable chemical formulations or less stable bubble (i.e. shell/gas) permutations and is advantageous in that relatively large microbubbles may be produced. The relatively larger microbubbles are discussed in greater detail below and are more effective in facilitating lysis than relatively smaller microbubbles. The microfluidic device 12' may be less than about 1 mm in largest transverse cross-section and therefore can be fit inside catheter 10, for example. The arrows indicate direction of flow of liquid 28A, 28B and gas 24. In at least one embodiment, microfluidic device 12' is manufactured using a lamination of polydimethylsiloxane (PDMS) (or similar silicone compositions), polymethylmethacrylate (PMMA), polyacrylamide, or polyimide layers making it flexible and capable of being rolled up within the tight cylindrical void of the catheter 10. In another embodiment, microfluidic device 12' is made of glass (e.g., Schott Borofloat 33), quartz or fused silica and is small enough that it does not need to be rolled to be placed into the void of the catheter distal tip portion 10D. The glass version is capable of operating at relatively higher pressures (compared to the PDMS embodiment) and therefore provides a relatively higher rate of production of microbubbles without the need for incorporating multiple microfluidic devices 12' in the catheter 10. In another embodiment, the microfluidic device 12' is manufactured using photoresist (SU-8, or similar) deposited on a solid substrate (glass, sapphire, silicon, etc.) and integrated directly into the catheter, thereby forgoing the need for additional process steps such as soft photolithography (as is required for polydimethylsiloxane (PDMS) device fabrication) or glass etching.

Figure 3A:
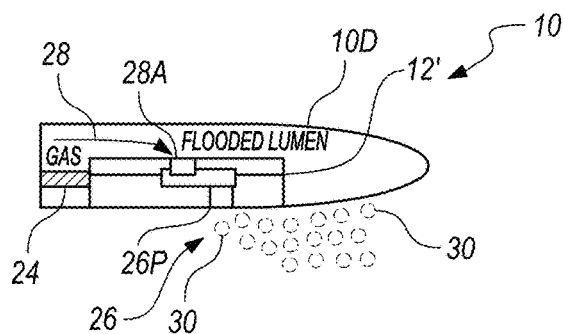
FIG. 3A is a schematic illustration of distal tip portion of a catheter having a microfluidics device installed therein, according to an embodiment of the present invention.

FIG. 3A is a schematic illustration of distal tip portion 10D of catheter 10 having microfluidics device 12' installed therein. In this embodiment, a flooded catheter design is used in which the microfluidics device 12' is immersed in liquid 28 that floods the void of the catheter tip portion 10D. Alternatively, liquid lines 28A, 28B could be provided to deliver the liquid into the device 12', like shown in FIG. 2. A gas line feeds into the microfluidics device to provide the gas stream 24. It is noted that liquid stream 28B is not visible in FIG. 3, but liquid stream 28A is shown. Further alternatively, the catheter 10 may be partitioned so that one compartment is flooded with liquid 28 and another compartment 24A is flooded with gas, as shown in FIG. 3B.

Figure 3B:
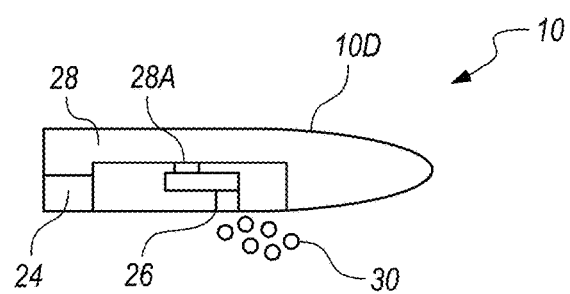
FIG. 3B is a schematic illustration of a microfluidics device installed in a distal tip portion of a catheter, wherein the microfluidics device is partitioned so that one compartment is flooded with liquid and another compartment is flooded with gas, according to an embodiment of the present invention.
Figure 3C:
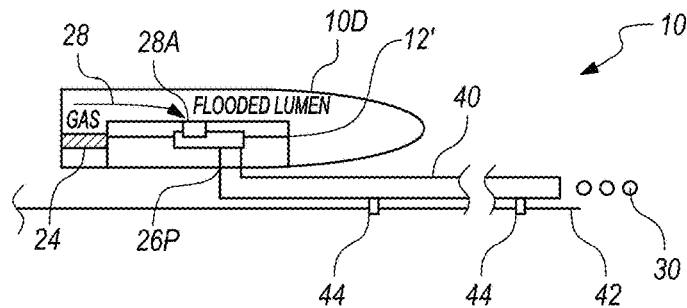
FIG. 3C schematically illustrates a narrow tube placed in fluid communication with an outlet port of a microfluidics device, according to another embodiment of the present invention.
Figure 3D:
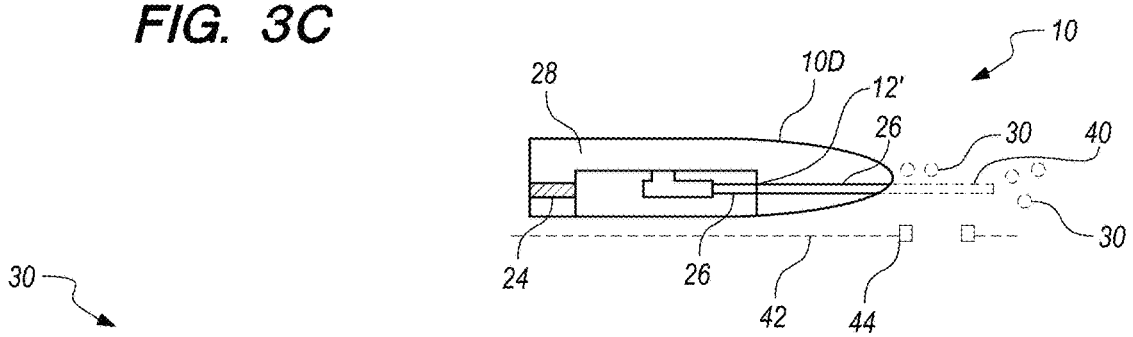
FIG. 3D schematically illustrates a microfluidics device installed in a distal tip portion of a catheter, wherein an outlet port of the microfluidics device is directed out of the distal tip of the catheter, according to another embodiment of the present invention.

In the embodiments shown in FIGS. 3A-3B, the microbubbles 30 exit the port 26P from nozzle 26, whereby microbubbles 30 are directly delivered to the vasculature and directed toward the blockage. Alternatively, a narrow tube 40 (e.g., less than or equal to about 3 F (1 mm)) can be placed in fluid communication with port 26P and extend distally of the distal tip of catheter 10 to provide the capability to output microbubbles 30 into smaller vessels than those that the distal end portion 10D of the catheter can enter, see FIG. 3C. Tube 40 can guide through the distal, smaller vessels to a site of occlusion by use of a guidewire 42 for example. Tube 40 can be configured with eyelets 44 or other guidance features configured to pass over the guide wire 42 so as to guide the tube 40 over the configuration of the guidewire. FIG. 3D illustrates an embodiment in which port 26 is directed out of the distal tip of the catheter 10. Optionally, this arrangement can be provided with tube 40 extending distally from the distal tip of the catheter 10.

Microbubbles 30 are produced with larger diameters than those that have been experimented with in the past. As noted above, microbubbles 30 preferably have diameters 30 in the range of about 8 to 25 micrometers. The ratio of microbubbles 30 having diameters in the range of about 8 to 25 micrometers to microbubbles having diameters less than about 8 micrometers should be at least 2.5/1. Ideally the microbubbles should be all the same size, which provides a more reliable and predictable response to a particular ensonification waveform. In reality, the microbubbles vary in size during initialization but once the system is initialized, it forms a steady stream of microbubbles all the same size, typically within about a 5% range of size variability. The present invention produces a stream of microbubbles of substantially the same size. However, the size of the microbubbles produced is programmable to a degree. The size of the microbubbles produced is a function of: the physical aperture size of the nozzle 26 in the microfluidics device 12' (foremost effect), the gas pressure and the liquid flow rate. Broadly speaking, increasing gas pressure increases microbubble size and increasing liquid flow rate reduces microbubble size, given a fixed aperture size. The larger diameters result in larger driving velocities of the microbubbles 30, compared to the velocities of smaller microbubbles driven by the same ultrasonic force. Further, the larger microbubbles are only problematic if they aggregate downstream after dissolution of the clot. By designing the microbubbles so that they dissolve or disintegrate within a short time after their production, this ensures that the microbubbles, after being applied to the clot, will dissolve or disintegrate shortly thereafter to as to eliminate the risk of accumulating downstream and causing problems. In one embodiment, microbubbles 30 comprising shells made from 3% albumin, 10% dextrose in 0.9% saline (i.e., 0.9% NaCl in water with 3% by weight albumin), the remaining 87% being 0.9% saline) and filled with $N_2$ gas yields a microbubble half-life of approximately twenty seconds. Replacing the $N_2$ with $CO_2$ shortens the half-life of the microbubble. The half-life values have been measured in the following ways: (1) direct observation of microbubble dissolution via light microscopy, (2) measuring microbubble concentration and size using a Coulter counter, (3) monitoring the intensity of the backscattered acoustic signal produced by a population of microbubbles as they dissolve. The term "half-life" is used here to denote the time it takes for half of the microbubbles to vanish and is independent of the method used to measure vanishment of the microbubbles.

The erosion (rate of removal) of a clot is dependent upon the amount of thrombolytic agent applied and the characteristics of the microbubbles and, optionally, ultrasonic driving force applied thereto. In general, as the concentration of thrombolytic agent increases, the erosion increases. However, the risk of hemorrhage also increases. The large microbubbles provided by the present invention increase the erosion of a clot, relative to application of smaller microbubbles using the same ultrasonic energy and concentration of thrombolytic agent.

Because of the design of the microbubbles of the present invention to dissolve shortly after use, these larger microbubbles can be effectively used to erode a clot. Because they are more effective, a relatively lower amount/concentration of thrombolytic agent can be used effectively, thereby lowering the risk of hemorrhage.

The microbubble gaseous core 34 (see FIG. 4) may be comprised of a single gas (e.g. nitrogen) or a mixture of gases (e.g. nitrogen, oxygen, carbon dioxide, mixtures of the same, or any of these in combination with one or more of the stable gases as described above) to alter microbubble stability and circulation lifetime.

The dissolution of the microbubbles is designed to occur as quickly as possible once the microbubbles 30 have passed the surgical target area, e.g., after erosion of the clot to the extent that the microbubble flows downstream thereof. Depending upon the blood flow conditions, the dissolution rate designed into the microbubbles can vary. For example, the half-life of the microbubbles is preferably less than thirty seconds, more preferably less than twenty seconds.

Figure 5:
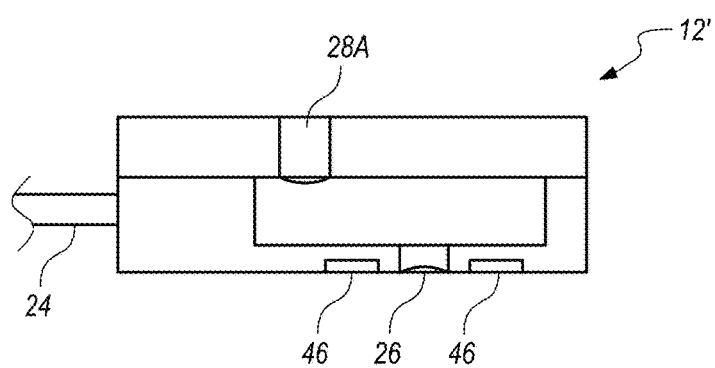
FIG. 5 schematically illustrates a microfluidic device provided with electrodes to function as a micro-Coulter device, according to an embodiment of the present invention.

Real-time feedback regarding the production rate and size of the microbubbles 30 may be achieved by incorporating monitoring technology directly into the microfluidic chip 12'. One preferred embodiment uses multiple nonpolarizing (e.g. AgCl) electrodes 46 (see FIG. 5) placed within the microfluidic device 12' that monitor the electrical resistance between two or more points within the device. Electrical resistance changes as microbubbles 30 are produced at the nozzle 26 and can be detected in a manner analogous to the "Coulter" principle. The micro Coulter arrangement, such as shown in FIG. 5, provides the ability to: monitor the operating conditions of the microfluidics device 12' during initialization of operation; count the production of microbubbles as they are formed; and calculate the diameters of the microbubbles produced.

Figure 6:
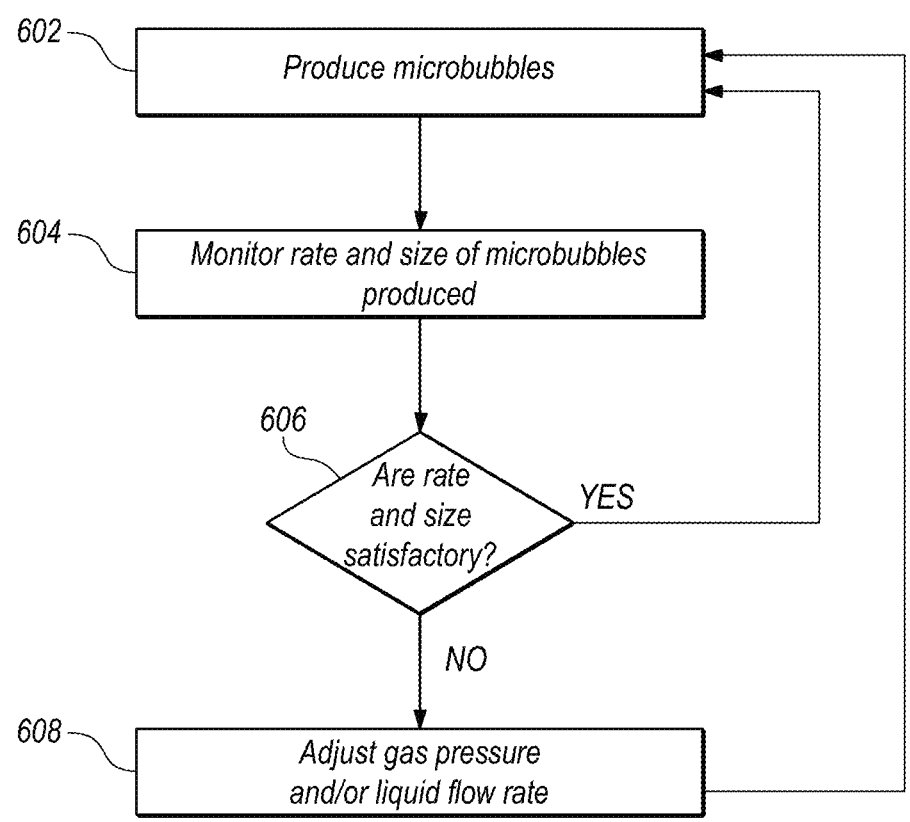
FIG. 6 illustrates events that may be carried out during a real-time feedback process, according to an embodiment of the present invention.

Real-time feedback supplied by the monitoring electrodes 46 may be incorporated into an automated feedback loop to adjust gas pressure and liquid flow rates to maintain stable microfluidic device operation. In addition, monitoring production rate will provide guidance on how many microbubbles 30 have been administered to the patient for dose reporting purposes. FIG. 6 illustrates an embodiment of real-time feedback, as described. At event 602 microbubbles are produced by the microfluidic device 12'. At event 604 monitoring is performed of at least one of the rate and size of the microbubbles produced. If at event 604 the rate and size are within the satisfactory predefined limits, then production of microbubbles continues in the same manner as before at event 602. If however, one or both of the rate and size are found at event 606 not to be satisfactory, then gas pressure and/or liquid flow rate is adjusted at event 608 and production of microbubbles continues with the adjusted gas pressure and/or liquid flow rate. This process may continue over the entire course of microbubble production to maintain stable microfluidic device 12' operation.

As noted above, as an alternative to the embodiment described with regard to FIG. 1, a more localized ultrasound source may be provided in the catheter 10, so that the ultrasound energy can be applied to the microbubbles from a location of the catheter, rather than from a location outside the patient. The more localized ultrasound source may comprise a transducer mounted within the catheter 10. The transducer may comprise one or more elements. It may comprise a phased array arranged in a longitudinal manner (like in the Siemens Acunav) or circumferentially as in IVUS arrays (Volcano IVUS). The transducer may be based upon piezoelectric principles (and comprise any known piezoelectric material—such as a PZT ceramic or a PMN-PT single crystal). Alternatively, it may be a silicon-based CMUT. The ultrasound can comprise any of several modes of use: Imaging B-Mode (fundamental or harmonic), Doppler (all Doppler modes—CW, PW, CDI, CDE), contrast specific imaging (pulse inversion, pulse amplitude modulation or the combination of the two). A single transducer element may be multi-modal (imaging+delivery) or separate elements may be used for each of imaging and delivery. Additionally, there may be a radiation force element, as described in U.S. application Ser. Nos. 12/739,129 and 13/306,391, for example.

Any of the embodiments described in U.S. patent application Ser. No. 12/739,128 (Now U.S. Pat. No. 8,622,911), Ser. Nos. 13/306,391 and 14/063,830 can be used in the present invention as an alternative to that described with regard to FIG. 1. U.S. patent application Ser. Nos. 12/739,128, 13/306,391 and 14/063,830 and U.S. Pat. No. 8,622,911 are hereby incorporated herein, in their entireties, by reference thereto.

Figure 7:
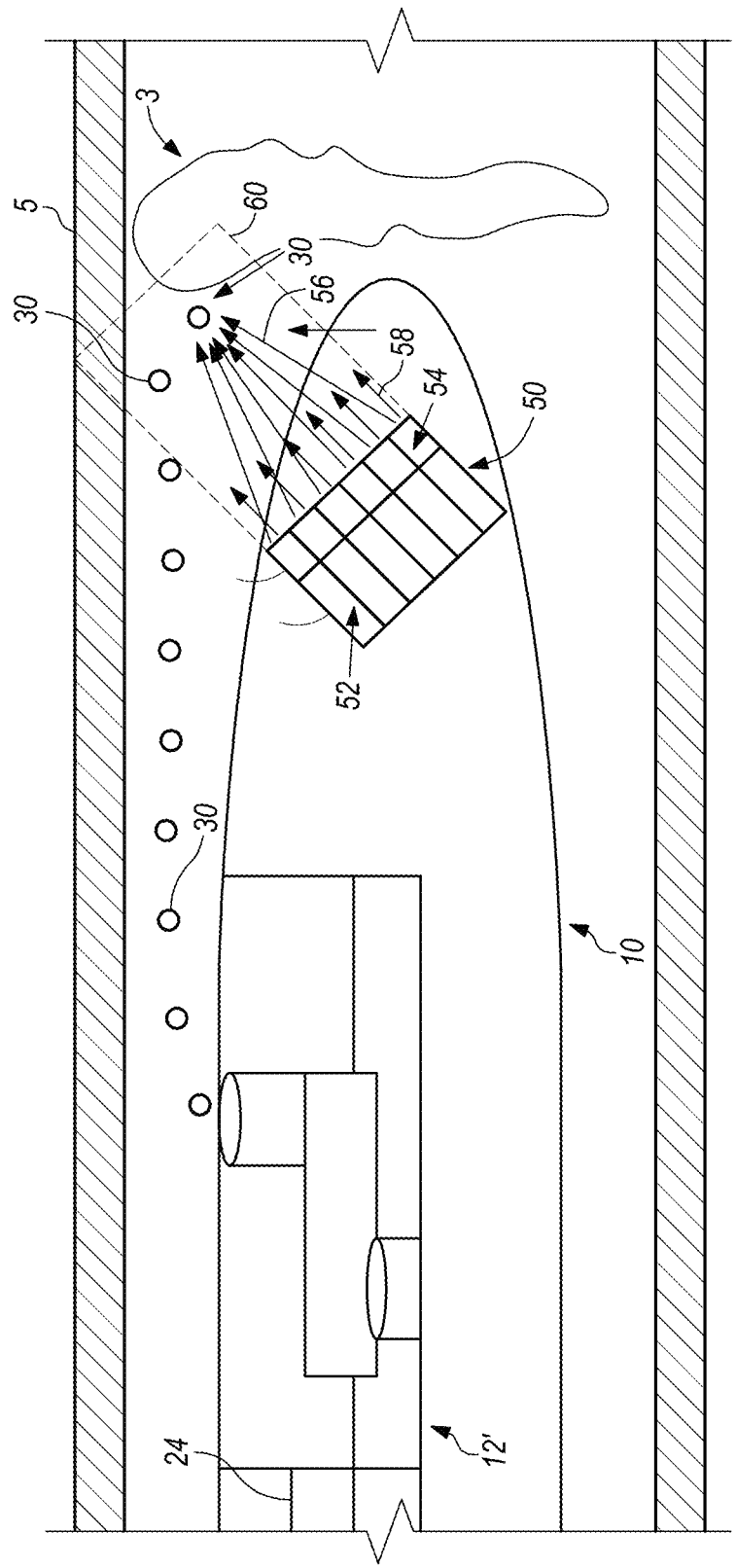
FIG. 7 schematically illustrates a partial view in which the catheter of the system includes an ultrasound transducer mounted therein for applying ultrasound energy to the surgical target site from a location within the catheter, according to an embodiment of the present invention.

FIG. 7 schematically illustrates a partial view of an embodiment of the present invention in which the catheter 10 of the system 100 includes an ultrasound transducer 50 mounted therein for applying ultrasound energy to the surgical target site from a location within the catheter 10. In the embodiment shown, transducer 50 comprises an array of relatively low frequency ultrasound transducer elements 52 and an array of relatively high frequency ultrasound transducer elements 54. The low frequency ultrasound energy 56 is focused at a location of or immediately adjacent to the surgical target area and applied to drive the microbubbles 30 into the surgical target area. In the example shown, the surgical target site or location is the location of the clot 3 in the cerebral artery 5. The high frequency ultrasound energy 58 is used for imaging of the surgical target area. The field of view provided by the high frequency ultrasound imaging is illustrated by reference numeral 60 in FIG. 7

Still referring to FIG. 7, the system 100 further comprises (although not shown) a control circuitry configured to send electrical activation to the ultrasound transducer arrays 52, 54, as well as other components and subsystems of the present invention, including, but not limited to the microfluidics device 12'. In addition to, or in lieu of providing ultrasonic radiation forces for translating the microbubbles 30 into or in the vicinity of the surgical target area, mechanical forces may be otherwise provided for translating the microbubbles 30 into or in the vicinity of the surgical target area.

It should be appreciated that the aforementioned catheter 10, microbubble reservoir or channel 12, 12' ultrasound transducer(s) 50, and controller may be disposed entirely inside the patient 1, or some components may be located outside of the patient 1, as already noted. The surgical target area is preferably within a cerebral artery, but could additionally or alternatively be in one or more arteries downstream of cerebral arteries; other blood vessels; an organ, including hollow organs and/or, solid organs; parenchymal tissue; stromal tissue; a tubular anatomical structure, including, but not limited to ducts.

The imaging transducer/transducer array 54 and the delivery/radiation force transducer/transducer array 52 may be identical. Whereas it is sometimes necessary to optimize two transducers for two functions it is also feasible, if the transducer possesses sufficient performance versatility (e.g. high frequency bandwidth and high power capability) to use the same transducer for both imaging and therapeutic function.

Another alternative that may be employed with any of the systems 100 described above, is to deliver the antithrombolytic agent directly from the catheter 10 rather than introducing the antithrombolytic agent systemically, such as through an intravenous drip. Further alternatively, rather than an IV drip or delivery directly from the catheter 10, the antithrombolytic agent can be dispensed into the carotid artery. These alternative approaches, involving dispensation of the antithrombolytic agent in the carotid artery or within the occluded vessel, will enable a further, potentially very significant, reduction in dosage of antithrombolytic agent that is required to be effective, with consequent reduced risk of intracerebral hemorrhage. The highly localized nature of drug delivery (using administration from the catheter 10) may enable the use of alternative antithrombolytic agents, such as previously investigated drugs that failed in trials due to side-effect risk (e.g. hemorrhage). Thus, "failed" drugs may potentially be resurrected if they are found to be relatively safe and effective at the lower dosage levels permitted by direct delivery through the catheter 10.

Figure 8:
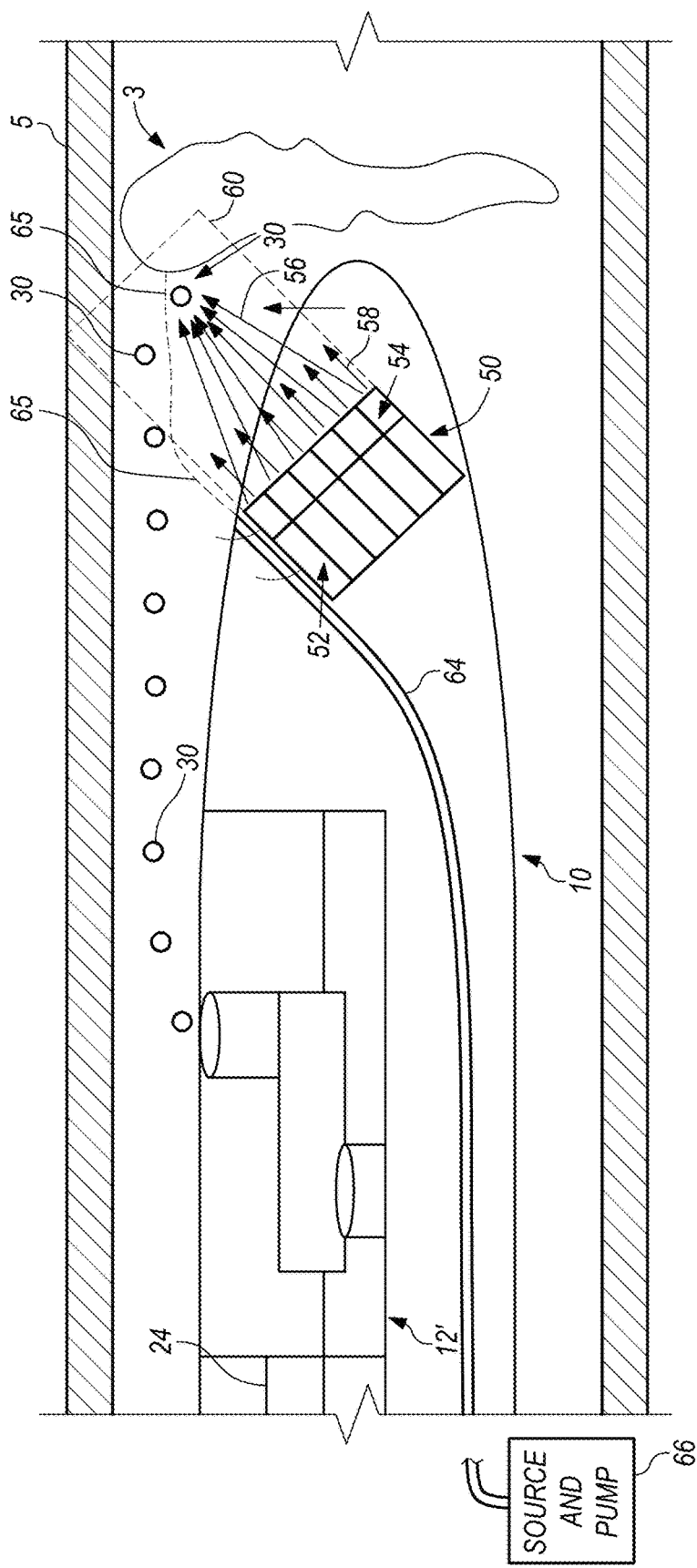
FIG. 8 schematically illustrates a partial view in which the catheter of FIG. 7 has been modified to provide direct delivery of an antithrombolytic agent, according to an embodiment of the present invention.

FIG. 8 schematically illustrates a partial view of an embodiment of the present invention in which the catheter 10 of the embodiment of FIG. 7 has been modified to provide direct delivery of an antithrombolytic agent. A tube or lumen 64 is provided to deliver the antithrombolytic agent 65 from a source 66, through at least a portion of the catheter 10 and out of the catheter toward the surgical target area. The source of antithrombolytic agent and pump/controlling circuitry may be provided outside of the patient 1, in fluid communication with the catheter 10, as in the embodiment of FIG. 8. Alternatively, one or more of the source, pump and circuitry may be provided inside the catheter 10 and, optionally, introduced into the patient 1 during use.

In at least one embodiment, any of the embodiments of system 100 described herein can be used in combination with a thrombectomy device. Examples of thrombectomy devices that can be used include, but are not limited to: the MERCI® retriever (Stryker Corporation, Kalamazoo, Mich.) (a shape metal alloy corkscrew-like device) and the PENUMBRA™ devices (Penumbra, Inc., Alameda, Calif.) (based upon an aspirator in combination with a small metal hook-like device to break apart a clot). During deployment of each of these devices, arterial flow is restricted by a proximally placed balloon—to minimize risk of embolism resulting from clot fragment being swept distal with respect to original clot position. Furthermore, the present systems 100 can be paired with other devices currently in development.

When applying ultrasound trans-cranially, optimum intensity of ultrasound energy applied to the microbubbles 30 to effect erosion of the clot will vary, depending upon the thickness of the patient's skull and the anatomy of the target region. In many cases, it is possible to cause a cavitation event to occur—i.e. to cause one or more microbubbles 30 to "explode". The sound produced by the explosion provides a one-way sound source from a single target location. The sound associated with the cavitation is akin to an ideal point acoustic source making it near perfect as a unique source upon which receive channel data can be processed. In this model, a single target source signal is known to come from a single point in the brain. However, the signal will be aberrated (time shifted) due to different path lengths in materials possessing different speeds of sound. The bone of the skull has a far higher speed of sound than soft tissue, and it is non-uniformly thick. Methods for processing the detected time of arrivals to calculate the required aberrating delay corrections (to be applied in either or both transmit and receive mode) are well known. For example, refer to: Dorny, "A self-survey technique for self-cohering of antenna systems" *Antennas and Propagation, IEEE Transactions on* (Volume: 26, Issue: 6) pp 877-881 1978, which is hereby incorporated herein, in its entirety, by reference thereto. More advanced phase aberration corrections approaches may also be used. These latter approaches are less onerous in terms of their need for a "beacon". For example, refer to the following article incorporated herein, in its entirety, by reference thereto: Flax and O'Donnell "Phase-aberration correction using signals from point reflectors and diffuse scatterers: basic principles" *IEEE Trans Ultrason Ferroelectr Freq Control.* 1988; 35(6):758-67.)

By applying a "micro dose" comprising a very small percentage of a conventional dose (e.g., a few thousands or a few tens of thousands) of microbubbles 30, there will be sufficient single microbubbles 30 in the field of view that each can be clearly differentiated—especially if using a nonlinear sensitive imaging technique such as those widely known in the field—e.g. pulse inversion, amplitude modulation or the combination "contrast pulse sequences". Once the signals from isolated microbubbles 30 are used as a beacon to calculate aberrating delays and these delays are superimposed in either or both transmit and receive modes, the system 100 can step into a mode wherein it incrementally increases transmit power until microbubble 30 destruction is observed to start occurring—i.e. a threshold effect. Since, as noted, destruction/explosion of microbubbles 20 is not preferred for the erosion applications described herein, the detection of the destruction threshold (the intensity level at which destruction/explosion of microbubbles substantially begins) allows the system 100 to back off from this threshold to some determined optimal level. For example, it may back off to 50% of the transmit power required to induce immediate microbubble 30 destruction, although some other predetermined percentage less than one hundred percent may be alternately programmed into the system 100, such as, but not limited to: 90%, 80%, 70%, 60%, etc. In this way, the system 100 rapidly determines an optimal phase aberrating correction and power setting that is precisely adaptive to a particular patient 1 and skull/target geometry. Once this calibration exercise is complete, the system 100 displays an indication that this step is complete (e.g. a "ready" light) and the user can dispense a full dose of microbubbles 30. At this time, the system 100 will operate at the optimal aberrating correction and power level to effect optimal, yet safe, thrombolytic drug delivery and clot lysis.

In at least one embodiment, side and/or forward-looking ultrasound imaging may be used to facilitate a fluoroscopy-free procedure. As one non-limiting example, transducer 50 of the embodiments of FIGS. 7 and 8 may be used to guide delivery and placement of the catheter 10, as well as to monitor the erosion procedure.

The system may be provided with dedicated ultrasound hardware. This is particularly relevant for embodiments where non ultrasound imaging is performed, but only driving, acoustic force is applied for microbubble and drug delivery. In these cases, the ultrasound instrumentation may comprise relatively inexpensive hardware to generate the requisite simple pulse shapes and intensities.

Figure 11A:
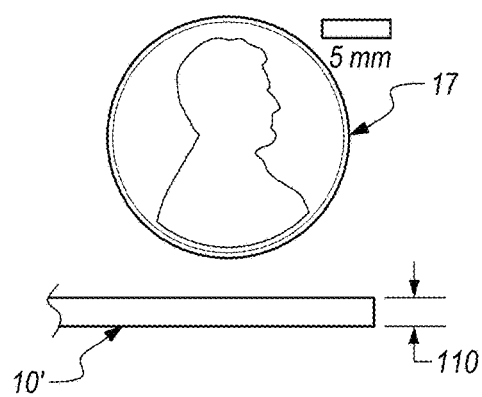
FIG. 11A shows a view of a distal end portion of a catheter according to an embodiment of the present invention, shown next to a penny for size comparison.

FIG. 11A shows a view of distal end portion of a catheter 10' according to an embodiment of the present invention, shown next to a penny for size comparison. In the embodiment shown, the distal end portion including the microfluidics device 12' has an outside diameter 110 of 2.5 mm. In another embodiment of catheter 10', outside diameter is 1.5 mm. In still another embodiment of catheter 10', outside diameter 110 is 1.0 mm. The microfluidics device 12' is molded from a micro-lithographically patterned photoresist using poly(dimethylsiloxane) (PDMS). A 1 mm diameter catheter 10' will allow the catheter 10' to be advanced at least as far as the M1 branch of the middle cerebral artery (MCA) in a pig or human, at least equaling the placement limit of a mechanical thrombectomy device. However, the microbubbles 30 produced will transit to downstream clots not addressable via mechanical devices, such as to M2 and M3 branches and beyond. Catheter 10' in this embodiment does not include an internal ultrasound source. In an alternative embodiment, the distal end portion of catheter 10' can be provided with side and/or forward looking ultrasound imaging capabilities so that catheter 10' can be inserted and placed without the need for fluoroscopy. In either case, catheter 10' can be employed in the system 110, for example as described with regard to FIG. 1, in substitution for catheter 10. Further optionally, catheter 10' may be configured to administer the thrombolytic agent from the distal end portion of catheter 10', either through a dedicated lumen, or by including the thrombolytic agent in the liquid streams of the microfluidics device 12'.

Catheter 10' is configured to produce and deliver microbubbles 30 via microfluidics device 12' at a rate of greater than or equal to 100,000 microbubbles per second, up to tens of millions of microbubbles per second, preferably in a range of 100,000 to 1,000,000 microbubbles per second, and having a diameter in the range of 10 μm-35 μm. Preliminary experimentation has indicated that 100,000 microbubbles/second is a sufficient production rate to produce a saturation level of microbubble deposition on a realistic size clot target (e.g., a clot target having a cross sectional dimension in the range from about 0.3 mm to about 3 mm, typically in the range from about 0.5 mm to about 2 mm). The microbubbles 30 can be assessed in terms of diameter and production rate using electrical impedance monitoring ("micro Coulter"). Microfluidics device 12' includes electrodes 1146 placed in the inlet ports (see FIG. 2) and a pair of electrodes 46 in the outlet to enable a "micro Coulter" monitoring device. Typically, heretofore microfluidics devices have been observed under a microscope until they produce a stable stream of microbubbles. In a clinical setting, the present invention provides microfluidics device 12' to be self-instrumented so that it can be paired with automated liquid and gas supplies so as to automatically turn on and regulate liquid flow/gas pressure to produce microbubbles at the desired diameter and production rate.

Figure 11B:
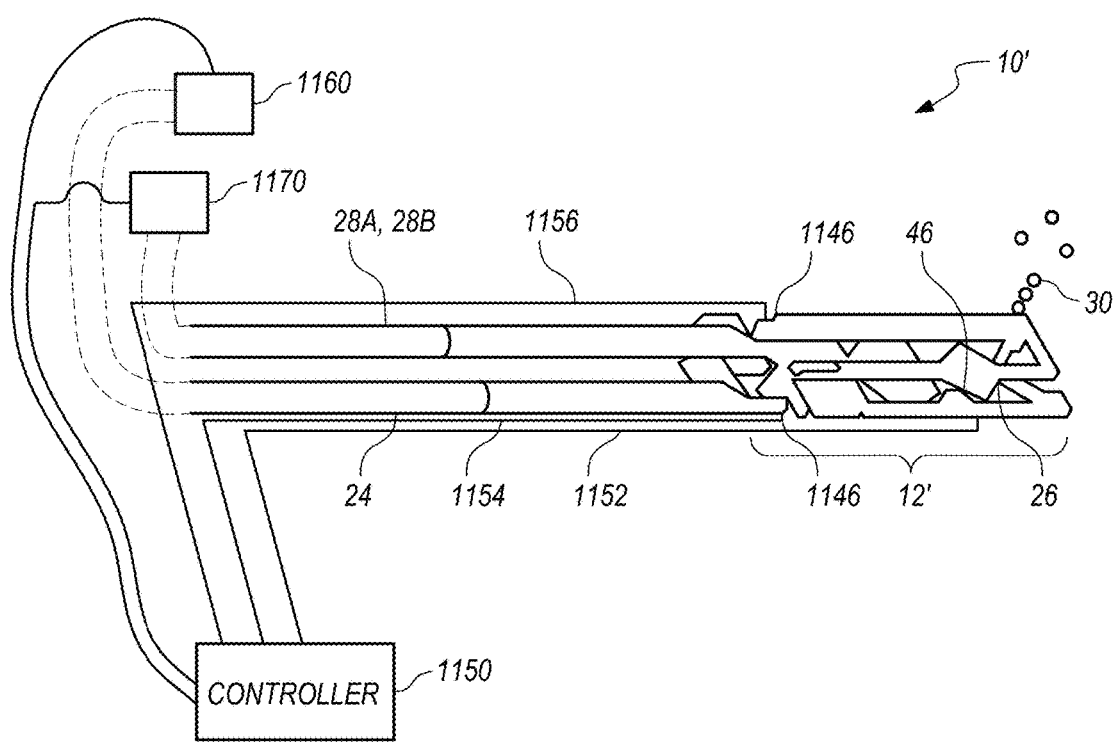
FIG. 11B schematically illustrates electrodes electrically connected to an external controller (computer), according to an embodiment of the present invention.
Figure 11C:
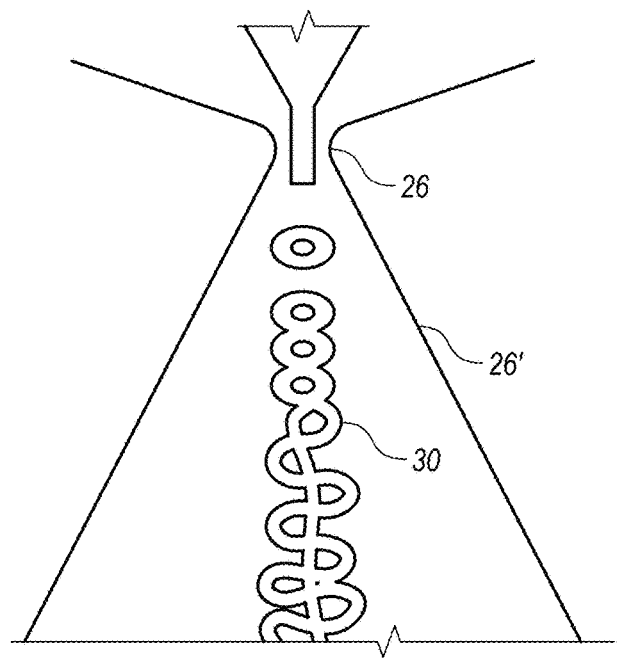
FIG. 11C illustrates a gas cone formed in the nozzle region of a microfluidics device during normal operation, according to an embodiment of the present invention.

FIG. 11B schematically illustrates electrodes 46, 1146 electrically connected to an external controller (computer) 1150. Additionally, controller 1150 is electrically connected to the gas supply pump/mechanism 1160 and liquid supply pump/mechanism 1170 that supply the gas and liquid to microfluidics device 12' respectively. Using Au, or Pt, plated electrodes 1146 placed in each of the liquid (saline-based) supply channels, various permutations of suboptimal operation can be detected so that gas and liquid pressure/flow parameters can be tuned so as to bring the device 12' into stable operation without the need for microscope visualization. In one embodiment, electrodes 1146 are co-planar electrodes (Au or Pt) and applied using a Cr/Ti adhesion layer During proper operation, there is a gas cone 26' in the nozzle region 26 (see FIG. 11C), resulting in an equal resistance between each of the two liquid inlets and the output channel. Additionally, there should no liquid in the gas inlet. Since the liquid is mainly mildly conductive, various fault conditions can be detected, e.g., in the event of device 12' flooding, the gas cone 26' vanishes and detectable impedance can be sensed between electrodes 1146 and 46 placed in the gas inlet and outlet channel, respectively. Unbalanced impedance between each of the two liquid inlets 1146 and the liquid in the outlet 46 denotes a second failure mode. Once a mode of failure is identified, the parameter tied to the specific failure mode can be adjusted in increments until steady-state operation occurs. Thus, there are two sets of designs for electrodes that can be used independently or together in a microfluidics device as described herein. A first set puts bulk type electrodes 1146 in the inlets (e.g., electrodes 1146 in one or both liquid inlets and in the in gas inlet) so as to detect, for example, channel flooding. During normal operation, there should be no saline/liquid in the gas inlet, so no electrical conduction occurs. If electrical conduction is detected at the gas inlet, then this indicates that a fault condition has occurred, typically flooding of the gas inlet with liquid (e.g., saline or whatever liquid is being used). The second set positions a set of adjacent electrodes 46 to form a Coulter sensing device. In this second set, the sensors (e.g., a pair of sensor strips, or the like) are placed closely adjacent to the gas bubble outlet, as described above.

Figure 11D:
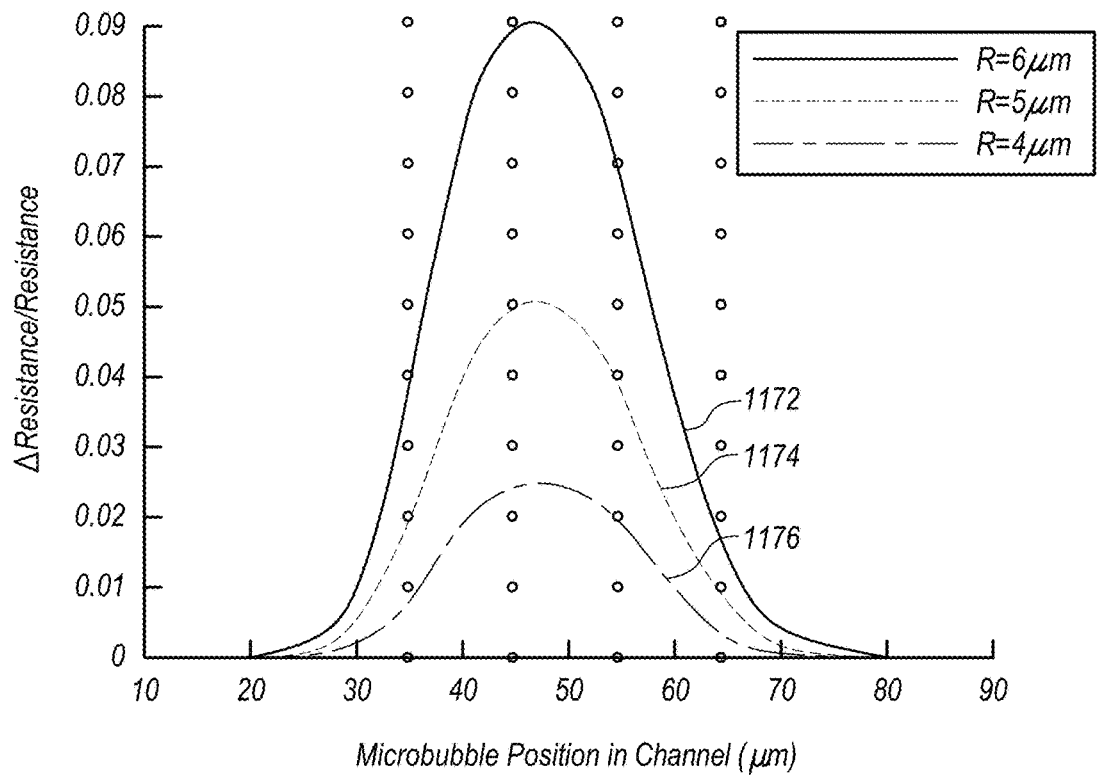
FIG. 11D shows the relationship between microbubble size and the resistance measured between electrodes in the vicinity of the microbubbles passing through a saline filled channel, according to an embodiment of the present invention.

FIG. 11D shows the relationship between microbubble 30 size and the resistance measured between electrodes 46 in the vicinity of the microbubbles passing through a saline filled channel. Curve 1172 shows the fractional resistance change that occurs as microbubbles of 6 μm diameter pass through the channel against their position relative to the electrodes 46 in the channel; and curves 1174 and 1176 show resistance change for microbubbles having 5 μm diameter and 4 μm diameter, respectively. Using this micro Coulter monitoring, it is shown that the diameter size of microbubbles 30 produced can be readily observed in real time, by measuring electrical impedance changes through the saline-based liquid phase present at the microfluidics aperture 26 near where microbubbles 30 break off and form a single-file stream of monodisperse microbubbles. On-chip measurements of microbubble size and production rates can be calibrated and validated against reference values acquired using a high-speed microscope camera.

When using a voltage >0.5 V, irreversible electrolysis can occur in the microchannels of the device 12', but higher frequencies (>500 kHz) can be used to avoid gas bubble formation in the microchannels. Additionally, platinum black can be used on the electrodes to decrease the double layer capacitance to diminish electrolytic effects.

Figure 14A:
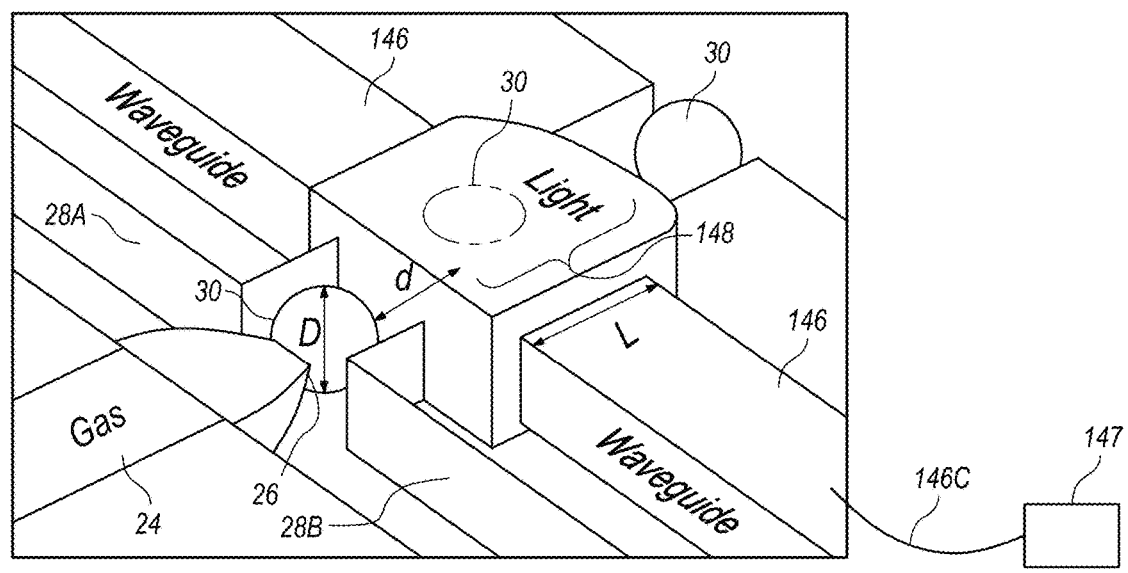
FIG. 14A is a three-dimensional schematic illustration of the microfluidic channel geometry with optical waveguides positioned on either side of the channel containing the microbubbles, according to an embodiment of the present invention.

Alternatively, optical waveguides operating in either transmission or reflection mode may be used to measure microbubble diameter and production rate. FIG. 14A is a three-dimensional schematic illustration of the microfluidic channel geometry with optical waveguides 146 positioned on either side of the channel containing the microbubbles 30. In FIG. 14A, light is transmitted into the channel by one waveguide 146 and is received on the other side of the channel by a second waveguide 146 that is connected by a fiber optic cable 146C to an optical detector 147. As microbubbles 30 are produced, they pass through the region 148 illuminated by light (e.g., green light, or any other wavelength of light may be used). The difference in refractive index between the liquid phase and the gaseous microbubble decreases the transmission of light across the channel. This change in transmittance is measured by the optical detector 147 and may be used to determine both the frequency of microbubble 30 transit across the illuminated region 148 and the size of each microbubble 30. Alternatively, a single waveguide 146 may be used in a reflection mode, in which light is transmitted into the channel by a single waveguide 146 and reflects off of the surface of the microbubble 30 back into the same waveguide 146. This single waveguide 146 is connected to a detector 147 by an optical fiber 146C, and changes in reflectance may be used to measure both the frequency of microbubble 30 transit across the illuminated region 148 and the size of the microbubble 30.

Figure 14B:
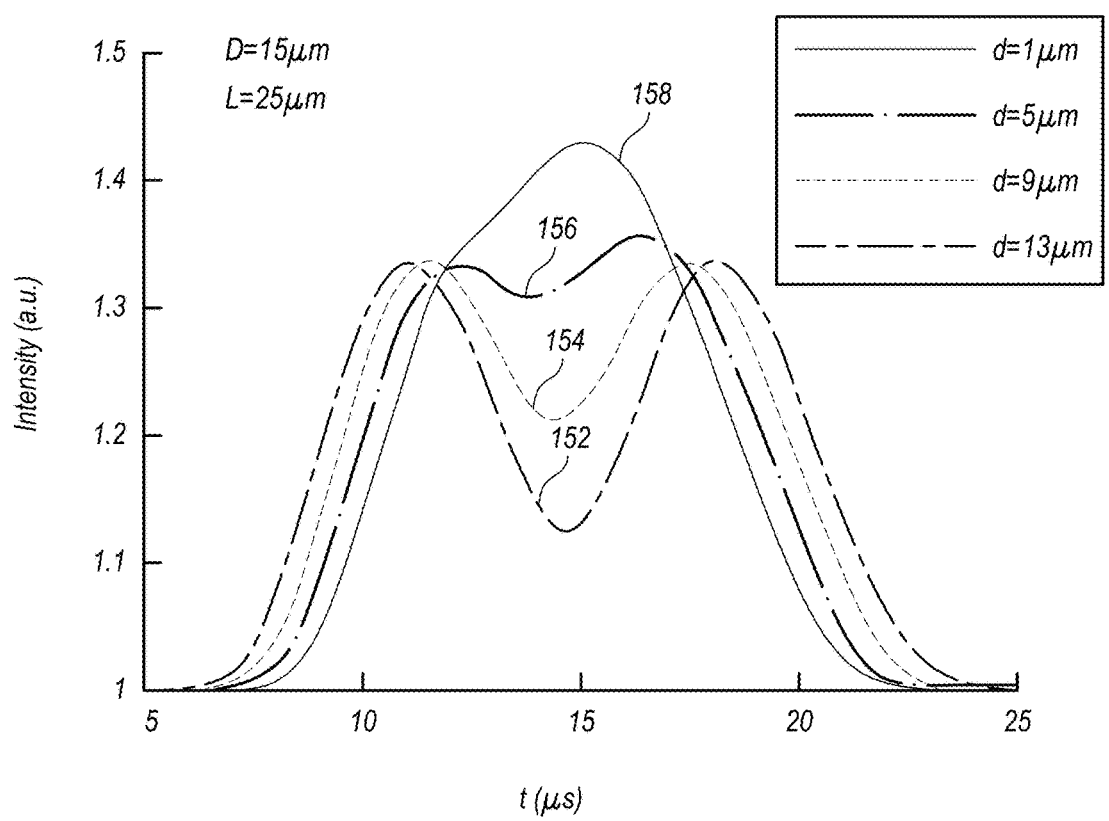
FIG. 14B shows simulated light reflectance measurements as two microbubbles pass sequentially through the illuminated section of the channel of FIG. 14A.

FIG. 14B shows simulated light reflectance measurements as two microbubbles 30 of 25 micrometer diameter pass sequentially through the illuminated section of the channel 152. "L=25 μm" refers to the length of the waveguide in the microfluidic chip. "D=15 μm" refers to the diameter of each microbubble 30 in the flow channel. The references to "d" refer to the distances (in microns) between neighboring microbubbles 30 in the flow channel. These distance are defined as the 'length' of liquid between the edges of neighboring microbubbles 30. Thus, the distances "d" do not measure the center-to-center distance between microbubbles, but the spacing between microbubbles 30. Curve 152 corresponds to the light intensity measured through time as two microbubbles 30 of 15 μm diameter pass by the waveguide (having a length L=25 μm) when the bubbles are separated by 13 μm length of liquid. Curves 154, 156 and 158 show the results as the spacing between the two microbubbles 30 is reduced to 9 μm, 5 μm and 1 μm, respectively. It can be observed that as the spacing is reduced from 13 μm to 1 μm, the resolution between the two peaks of the curve gradually makes it so the two peaks are indistinguishable. Thus, at spacing d=1 μm, it is no longer possible to distinguish between the two microbubbles 30 and thus it is not possible to detect, count, or size individual microbubbles 30.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

A catheter based-system employing a microfluidics device 12' in a catheter having an outside diameter of 2 mm and a length of 2 m, with the tubing of the catheter being made of PE50 and having a 250 um inside diameter was developed and tested. The microfluidics flow-focusing device 12' produced microbubbles 30 having albumin shells and nitrogen cores, using 3% albumin, 10% dextrose in 0.9% saline with $N_2$ gas. The microbubbles 30 were delivered out of the port 26 of the microfluidics device 12' and out of the catheter for over thirty minutes. It is believed that thirty minutes should be a good approximation of the time required for a catheter based clot disintegration procedure in vivo. The microbubbles produced were large, having diameters in the range of about 5 μm to about 20 μm that, by design, dissolved rapidly after production. For in vivo administration, this will mitigate the risk of emboli in small, downstream capillary blood vessels and/or other downstream vessels or locations.

Figure 9A:
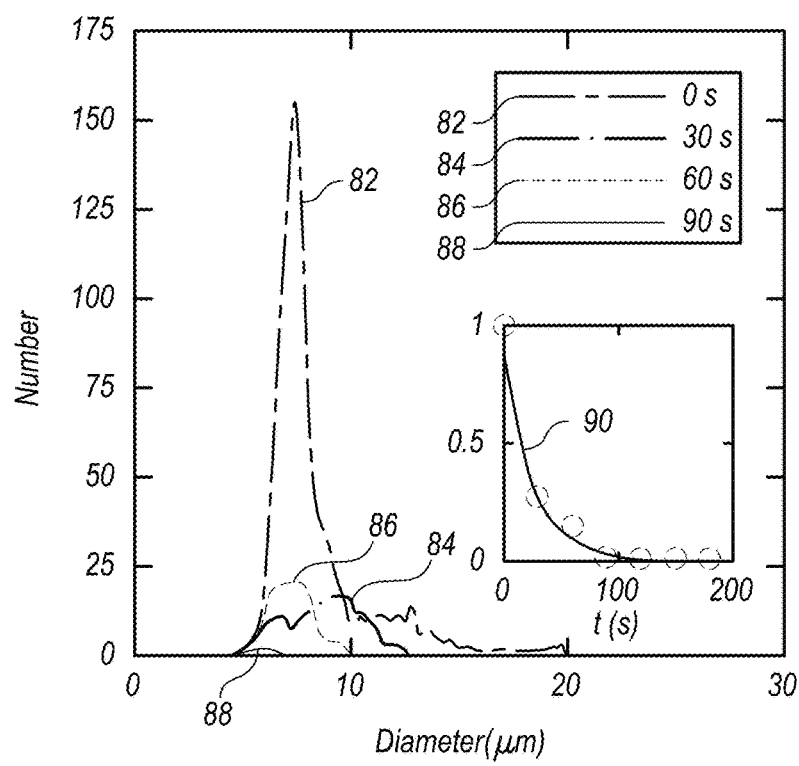
FIG. 9A shows size distributions and numbers of microbubbles at various times after application of microbubbles to a target, according to an embodiment of the present invention.

The large microbubbles produced yield greater bioeffects than those of smaller diameter (e.g., 2 μm average), and, because of their predesigned low stability (rapid dissolution after production) will increase the rate of clot lysis (relative to a similar treatment using 2 μm average diameter microbubbles), without the increased risk of embolism downstream. FIG. 9A shows the size distributions of microbubbles 30 for zero seconds 82, thirty seconds 84, sixty seconds 86 and ninety seconds 88, with the x-axis showing the microbubble diameters and the y-axis showing the number of microbubbles. The number of microbubbles are counted at 0.05 μm intervals, so the curve must be integrated to determine the total number of microbubbles produced. A typical run measured ~50,000-100,000 microbubbles produced. The inset shows the time decay 90 of the total number of microbubbles (normalized to a scale of zero to one on the y-axis, with time in seconds on the x-axis). From the insert, it can be observed that all microbubbles 30 have dissolved after about ninety seconds.

Figure 9B:
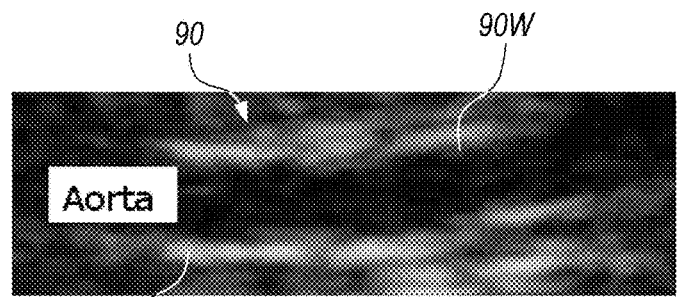
FIG. 9B shows a B-Mode (anatomic mode) ultrasound image of an aorta of a mouse prior to administration of microbubbles.
Figure 9C:
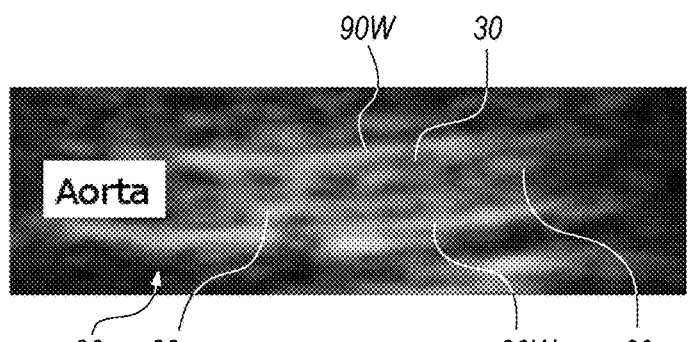
FIG. 9C shows a B-Mode (anatomic mode) ultrasound image of large microbubbles having been produced in the aorta of FIG. 9B, according to an embodiment of the present invention.

FIG. 9B shows a B-Mode (anatomic mode) ultrasound image of an aorta 90 of a mouse prior to administration of microbubbles therein. FIG. 9C shows a B-Mode (anatomic mode) ultrasound image after administration of the microbubbles, showing the large microbubbles 30 having been produced in the aorta 90 of the mouse according to the above example. The present invention has thus enabled, for the first time, in vivo administration of large microbubbles without adverse side effects in murine models.

Example 2

Figure 10A:
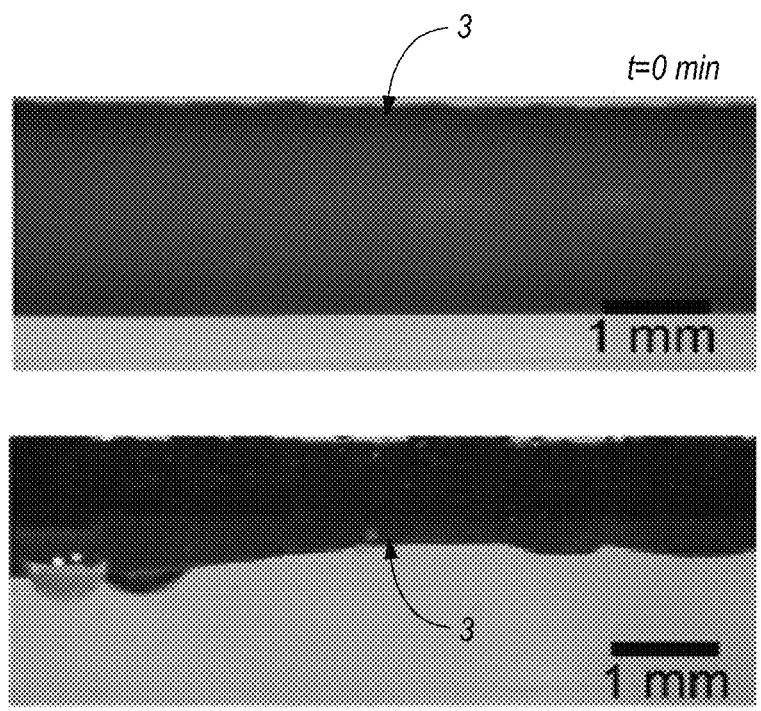
FIG. 10A shows a magnified plan view of a blood clot in a clear thin walled plastic tube before and after treatment with tPA, ultrasound and microbubbles, according to an embodiment of the present invention.
Figure 10B:
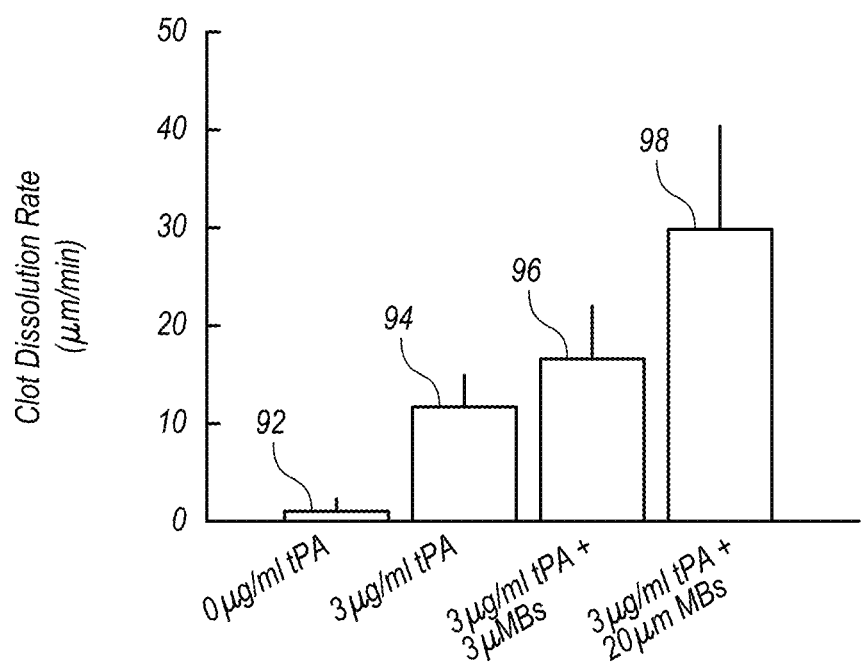
FIG. 10B shows results of in vitro clot lysis studies that show that the microbubbles of an embodiment of the present invention exceed the performance of smaller microbubble formulations for enhancing tPA efficacy and clot lysis rates.

FIG. 10A shows a magnified plan view of a blood clot in a clear thin walled plastic tube before and after treatment with tPA, ultrasound and microbubbles. In the top image there is the full size unmodified (untreated) clot 3. In the bottom image, it is evident that the clot 3 has been eroded away from the lower surface towards the upper surface in response to tPA, microbubbles 30 and ultrasound operating on the slowly eroded away surface. This experiment was performed to quantify mean "erosion rate" in microns/minute. FIG. 10B compares the erosion responses obtained with 1) no tPA ("control"), 2 tPA (no ultrasound and no microbubbles) 3) tPA+ultrasound+standard (small) microbubbles and 4) tPA+ultrasound+large (20 micron diameter) microbubbles 30. The ultrasound condition was 1 MHz frequency, 30% duty cycle and 200 kPa Peak Negative Pressure (PNP). However, modest variations in the acoustic parameters will result in similar trends. The tPA concentration, when used, is 3 micrograms/ml. However, other tPA concentrations are also feasible.

FIG. 10B shows results of in vitro clot lysis studies that show that the transiently stable, large, microbubbles 30 exceed the performance of smaller microbubble formulations for enhancing tPA efficacy and clot lysis rates by a statistically significant margin. The studies were conducted in human plasma having a flow velocity of 5 cm/s. The ultrasound was applied with a 1 MHz center frequency, 200 kPA PNP, 30% duty cycle. tPA was applied at a concentration of approximately 3 μg/mL and the ultrasound was applied for about one hour. The initial clot diameter was in the range of about 1.7 mm to 2.3 mm. The control rates of erosion measure were consistent with those in the previous literature. FIG. 10B shows that the ultrasound applied to the clot with no microbubbles and no tPA applied 92 resulted in an erosion rate of the clot of about 1 μm/min; the application of tPA at 3 μg/mL, but no microbubbles applied 94 resulted in an erosion rate of the clot of about 11 μm/min; the application of tPA at 3 μg/mL with microbubbles having an average diameter of 3 μm resulted in an erosion rate 96 of about 16 μm/min, and the application of tPA at 3 μg/mL with microbubbles 30 having an average diameter of 20 μm resulted in an erosion rate 98 of about 28 μm/min Example 3

In a prior art example, microbubbles having a lipid shell and sulfurhexafluouride gas with a concentration in the range of 2 to $5 \times 10^8$ microbubbles/ml and mean diameter of 2.5 μm and recombinant tissue plasminogen activator (rt-PA) at a concentration of 0.3 mg/ml were delivered through a 140 cm long catheter having 0.45 mm diameter inner lumen, to a clot formed in a polyimide tube having a 6 mm inner diameter. Ultrasound was delivered to the clot over a ten minute treatment period with peak rarefaction acoustic pressure of 2.1 MPa and a duty cycle of 4%. The microbubbles and rt-PA were concurrently delivered over a period of two minutes at a flow rate of 18 ml/h. After the treatment period, the clot was removed and weighed to determine a clot lysis percentage expressed as a percentage of the clot weight after the procedure, as compared to the clot weight prior to the procedure. Clot lysis percentage approached 60%. Further details of this example can be found in Soltani et al., "Potentiating intra-arterial sonothrombolysis for acute ischemic stroke by the addition of the ultrasound contrast agents", J Thromb Thrombolysis, 2011 January; 31(1):71-84, which is incorporated herein, in its entirety, by reference thereto.

Example 4

In an example according to an embodiment of the present invention, microbubbles having a 3% albumin and 10% dextrose shell and $N_2$ gas with a concentration in the range of 50,000 microbubbles/ml and mean diameter of 20 μm and recombinant tissue plasminogen activator (rt-PA) at a concentration of 3 mg/ml were delivered through a 20 cm long catheter comprised of PE50 tubing, to a clot formed in a transparent PTFE tube having a 4 mm inner diameter. Ultrasound was delivered to the clot over a 30 minute treatment period with 200 kPA peak negative pressure, frequency of 1 Mhz and duty cycle of 30%. The microbubbles and rt-PA were concurrently delivered over a period of 30 minutes at a flow rate of 12 ml/min Throughout the treatment period, clot diameter was monitored microscopically. Peak clot erosion rates of approximately 30 um/min were recorded, as compared to 10 um/min when using 3 mg/ml (rt-PA) alone.

Example 5

Figure 12A:
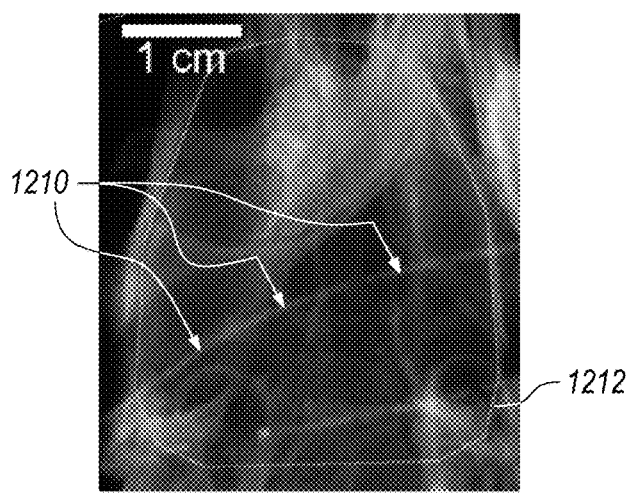
FIG. 12A shows a dental X-ray image of a rat skull showing a 750 µm diameter 5% w/v barium clot.
Figure 12B:
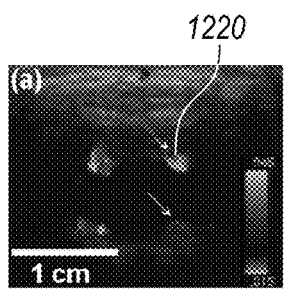
FIGS. 12B-12G show Color Doppler images of the rat MCA of the brain shown in FIG. 12A.
Figure 12C:
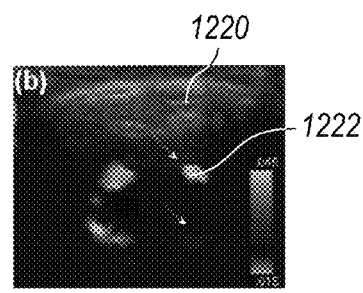
Figure 12D:
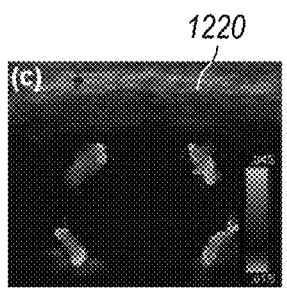
Figure 12E:
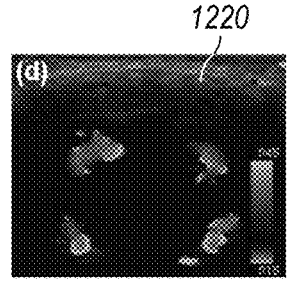
Figure 12F:
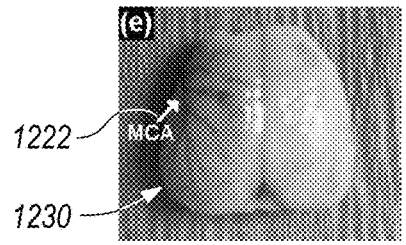
Figure 12G:
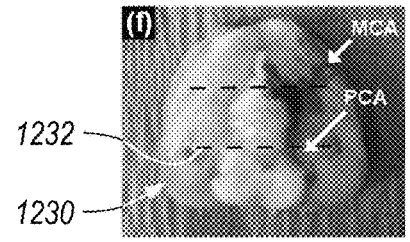

Color Doppler imaging using a high frequency clinical scanner provides valuable real-time guidance on the evolution and location of a stroke in the rat brain. FIG. 12A shows a dental X-ray image of a rat skull showing a 750 μm diameter 5% w/v barium clot 1210. The outline of the brain cavity is shown at 1212. FIGS. 12B-12G show Color Doppler images of the rat MCA of the brain shown in FIG. 12A. FIG. 12B shows the MCA prior to formation of a clot. FIG. 12C shows clot 1222 present in the MCA. FIG. 12D again shows the absence of clot 1222 confirming that the clot 1222 has been disintegrated. FIG. 12E is an image of the MCA having had blood flow restored. FIG. 12F shown the excised brain 1230 with an indication of the location of the clot 1222 in the MCA 1220 vessel tree. FIG. 12G shows the Circle of Willis 1232 of the brain 1230.

Preliminary clot erosion data was obtained using an Olympus/Panametrics 1 MHz V303-SU transducer. For determining clot erosion according to an embodiment of the present invention, a 5 mm diameter, 1 MHz transducer with a 15 mm nominal focus will be used. The offset from the center of the imaging plane from the center of the delivery transducer will be recorded and used so that once a desired image plane (or sequence of planes) is established, the translation offset is compensated for precisely to assure reliable ensonification of the desired tissue region. A stepper-controlled translation stage will be used to enable precise, repeatable, scanning of the high frequency imaging array. The paired imaging and Panametrics transducers will be mounted in a 3D printed plastic holder.

Example 6

Varying gas composition of the microbubbles 30, versus the gas in surrounding liquid, affects microbubble 30 stability. Currently, the least stable microbubbles of the present invention have a half-life of <20 s. The stability can be varied, as noted above, by modifying the gas composition inside the microbubbles. For example, by choosing a highly stable gas with low rate of diffusion (e.g., $C_4F_{10}$), longevity of several minutes is achievable. Adding $O_2$, or $N_2$, will decrease longevity. Adding or increasing $CO_2$ will provide microbubbles 30 having the shortest half-lives. Increasing $C_4F_{10}$, (or $C_3F_8$) will increase half-life. The shell composition can also be altered to change half-life performance. In one example, shell composition contains 3% albumin, 10% dextrose.

Example 7

Figure 13:
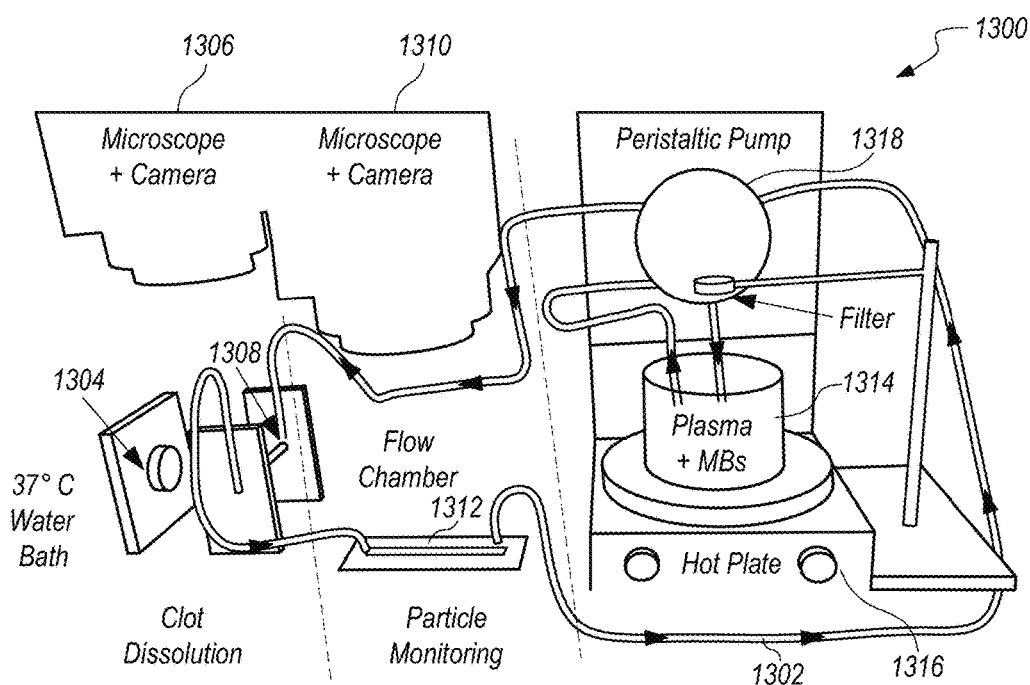
FIG. 13 schematically illustrates an in vitro experimental apparatus according to an embodiment of the present invention.

The clot formation and erosion process is highly complex and dependent on many interconnected factors. An in vitro human blood clot model was developed to assess clot erosion based on the following measurements: (1) linear erosion rate (μm/min) derived from microscopic images; (2) relative volumetric erosion rate derived from colorimetric quantification of red blood cells released from the clot; (3) fibrinolysis rates derived from the release of Fluorescein isothiocyanate (FITC_-labeled fibrinogen incorporated within the clot, and (4) microscopic video evaluation of clot "break-off" fragment size. The in vitro experimental apparatus 1300 is shown in FIG. 13. Blood clots will be formed by adding FITC-labeled fibrinogen to recalcified human whole blood and incubated at 37 C for three hours. A single clot will be placed in a flow loop 1302 through which human plasma, tPA, and/or microbubbles 30 will be circulated. A container 1314 of the human plasma, tPA and/or microbubbles 30 is maintained at a predetermined temperature, such as 37 C, by a temperature-controllable hot plate 1316, and the contents of container 1314 are circulated through the loop by peristaltic pump 1318. Ultrasound will be applied to the clot using a Panametrics transducer 1304, and images of macroscopic clot erosion will be captured by a microscope and camera 1306 placed above the clot 1308. A second microscope and video camera 1310 will be placed above a small flow chamber 1312 located downstream of the clot 1308 in order to monitor for the presence of clot fragments. Preliminary testing with beads of known size indicated adequate detection sensitivity down to approximately 40 μm particle diameter. 5 μl samples of the circulating plasma will be acquired every 30 seconds, and red blood cell (RBC) and FITC-fibrinogen release from the clot 1308 will be measured by optical absorption and fluorescence emission assays. This system 1300 provides multiple outputs through which clot degradation, ultrasound, and microbubble parameters may be studied. The large number of variables and potential ranges for each variable precludes a full factorial study of all parameters. Therefore, our baselines for each experiment will be derived from previous sonothrombolysis literature and our own preliminary data.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A method of treating a treatment site in a patient, said method comprising:
   inserting a catheter into the patient;
   delivering microbubbles generated by a microfluidics device provided in the catheter, toward the treatment site in the patient, wherein the microfluidics device generates the microbubbles by focusing a gas stream at a nozzle by two liquid streams; and
   applying ultrasonic energy to the microbubbles to vibrate the microbubbles.

2. The method of claim 1, wherein the microbubbles are designed such that at least 50 percent of the microbubbles dissolve, without application of the ultrasonic energy, within 120 seconds after production of the microbubbles.

3. The method of claim 1, wherein the microbubbles are designed such that at least 30 percent of the microbubbles dissolve, without application of the ultrasonic energy, within 120 seconds after production of the microbubbles.

4. The method of claim 1, wherein the microbubbles are designed such that at least 90 percent of the microbubbles dissolve, without application of the ultrasonic energy, within 120 seconds after production of the microbubbles.

5. The method of claim 1, wherein the microbubbles are designed such that microbubbles reduce in size by at least 50 percent, without application of the ultrasonic energy, within 120 seconds after production of the microbubbles.

6. The method of claim 1, wherein the microbubbles are designed such that the microbubbles reduce in size by at least 30 percent, without application of the ultrasonic energy, within 120 seconds after production of the microbubbles.

7. The method of claim 1, wherein the microbubbles are designed such that the microbubbles reduce in size by at least 90 percent, without application of the ultrasonic energy, within 120 seconds after production of the microbubbles.

8. The method of claim 1, wherein the microbubbles are designed such that at least 80 percent of a total volume of the microbubbles vanishes, without application of the ultrasonic energy, after a time period in the range of from 30 seconds to 180 seconds after production of the microbubbles.

9. The method of claim 8, wherein the microbubbles are designed such that at least 80 percent of the total volume of microbubbles vanishes, without application of the ultrasonic energy, after 120 seconds after production of the microbubbles.

10. The method of claim 1, the microbubbles are designed such that wherein at least 50 percent of a total volume of the microbubbles vanishes, without application of the ultrasonic energy, after a time period in the range of from 30 seconds to 180 seconds after production of the microbubbles.

11. The method of claim 10, wherein the microbubbles are designed such that at least 50 percent of the total volume of the microbubbles vanishes, without application of the ultrasonic energy, after 120 seconds after production of the microbubbles.

12. The method of claim 1, wherein the microbubbles are designed such that at least 30 percent of a total volume of the microbubbles vanishes, without application of the ultrasonic energy, after a time period in the range of from 30 seconds to 180 seconds after production of the microbubbles.

13. The method of claim 12, wherein the microbubbles are designed such that at least 30 percent of the total volume of the microbubbles vanishes, without application of the ultrasonic energy, after 120 seconds after production of the microbubbles.

14. The method of claim 1, wherein the microbubbles are designed such that at least 90 percent of the microbubbles dissolve, without application of the ultrasonic energy, after a time period in the range of 30 seconds to 180 seconds after production of the microbubbles.

15. The method of claim 1, wherein the microbubbles are designed such that at least 80 percent of the microbubbles dissolve, without application of the ultrasonic energy, after a time period in the range of 30 seconds to 180 seconds after production of the microbubbles.

16. The method of claim 1, wherein the microbubbles are designed such that at least 30 percent of the microbubbles dissolve, without application of the ultrasonic energy, after a time period in the range of 30 seconds to 180 seconds after production of the microbubbles.

17. The method of claim 1, wherein the microbubbles are designed such that at least 50 percent of the microbubbles dissolve, without application of the ultrasonic energy, within a predetermined time period after production of the microbubbles, wherein said predetermined time period is in the range of 30 seconds to 180 seconds.

18. The method of claim 1, wherein the microbubbles are designed such that all of the microbubbles dissolve, without application of the ultrasonic energy, within ninety seconds after production of the microbubbles.

19. The method of any one of claims 1-18, wherein the microbubbles have an average diameter greater than or equal to about eight micrometers.

20. The method of claim 1, wherein the microbubbles have an average diameter greater than or equal to about twenty-five micrometers.

21. The method of claim 20, wherein the average diameter is in the range of twenty-five to thirty-five micrometers.

22. The method of claim 1, wherein the microbubbles have an average diameter in the range of about eight micrometers to about twenty-five micrometers.

23. The method of claim 1, wherein the microbubbles have an average diameter in the range of about ten micrometers to about twenty micrometers.

24. The method of claim 1, wherein the microbubbles have an average diameter in the range of about eight micrometers to about twenty micrometers.

25. The method of claim 1, wherein the microbubbles each have a-shell comprising albumin and a core comprising nitrogen.

26. The method of claim 1, wherein the microbubbles each have a shell and a core, and wherein said core comprises an unstable gas.

27. The method of claim 26, wherein said core further comprises a stable gas.

28. The method of claim 26, wherein said core further comprises a neuroprotective gas.

29. The method of claim 27, wherein said core further comprises a neuroprotective gas.

30. The method of claim 1, wherein the treatment site comprises a blood clot in the brain of the patient and the ultrasonic energy is delivered trans-cranially from a location outside of the cranium.

31. The method of claim 1, wherein the treatment site comprises a blood clot in a cerebral artery and the catheter is inserted into the cerebral artery.

32. The method of claim 1, wherein the treatment site comprises a blood clot in a blood vessel, having caused an ischemic stroke.

33. The method of claim 1, wherein the treatment site comprises a blood clot comprising congealed blood resulting from a hemorrhage.

34. The method of claim 1, wherein the treatment site comprises a blood clot in a vein, having caused deep vein thrombosis.

35. The method of claim 1, wherein the treatment site comprises a blood clot in a pulmonary artery, having caused a pulmonary embolism.

36. The method of claim 1, wherein the microfluidics device is located within a distal end portion of the catheter.

37. The method of claim 36, wherein the microfluidics device is inserted into the patient along with the catheter.

38. The method of claim 1, wherein the treatment site comprises a blood clot in the brain of the patient and the ultrasonic energy is delivered from the catheter.

39. The method of claim 1, wherein the ultrasonic energy is delivered from a location outside the body of the patient to a location inside the patient at or near a location of the treatment site.

40. The method of claim 1, wherein the ultrasonic energy is delivered from the catheter.

41. The method of claim 1, further comprising real-time monitoring at least one of production rate and size of microbubbles produced.

42. The method of claim 41, wherein said real-time monitoring is performed in an automatic feedback loop, said method further comprising automatically adjusting at least one of gas pressure, gas flow rate, liquid pressure and liquid flow rate to maintain stable production rate and size of the microbubbles.

43. The method of claim 1, wherein the treatment site comprises a blood clot, said method further comprising concurrent or adjacent use of a thrombectomy device to assist in at least one of breaking up the blood clot and removing the blood clot.

44. The method of claim 1, wherein said delivering microbubbles and applying ultrasonic energy comprise:
  initially delivering a microdose of the microbubbles;
  receiving ultrasound echo signals from one or more isolated microbubbles;
  calculating aberrating delays based upon the ultrasound echo signals received from the one or more isolated microbubbles; and
  superimposing the aberrating delays on at least one of transmit and receive phases of the ultrasonic energy.

45. The method of claim 1, further comprising:
  incrementally increasing power of a transmit ultrasound energy to determine a threshold power level wherein microbubble destruction is observed to start occurring;
  reducing the power of the transmit ultrasound energy to a reduced power level comprising a predetermined percentage of the threshold power level; and
  delivering the microbubbles at full dose and applying the ultrasonic energy to the microbubbles at the reduced power level.

46. The method of claim 1, wherein a frequency of the ultrasonic energy is matched to a resonance frequency of the microbubbles.

47. The method of claim 1, wherein a frequency of the ultrasonic energy is set off-resonance relative to a resonance frequency of the microbubbles such that said frequency of said ultrasonic energy differs from said resonance frequency.

48. The method of claim 1, wherein the method is carried out and monitored using ultrasound imaging, without any use of fluoroscopy or X-ray imaging.

49. The method of claim 1,
  wherein said microfluidics device comprises an outlet port from which said microbubbles are outputted, and
  wherein a distance from said outlet port to the treatment site is 5 cm or less.

50. The method of claim 49, wherein said distance is in the range of 2 cm to 4 cm.

51. The method of claim 1, wherein a blood clot is located at the treatment site.

52. The method of claim 1, further comprising delivering a thrombolytic agent toward the treatment site.

53. The method of claim 52, wherein the thrombolytic agent is delivered intravenously.

54. The method of claim 52, wherein said delivering a thrombolytic agent comprises introducing the thrombolytic agent into a carotid artery of the patient.

55. The method of claim 52, wherein said delivering a thrombolytic agent comprises delivering the thrombolytic agent from a distal end portion of the catheter.

56. The method of claim 52, wherein the thrombolytic agent comprises tissue Plasminogen Activator (tPA).

57. The method of claim 1, wherein the microbubbles need only to survive a few seconds before delivery to the treatment site.

58. The method of claim 1, wherein said microbubbles have a half-life less than three minutes and are designed to dissolve within a short time after production, whether or not ultrasonic energy is applied, said time being sufficiently short to reduce the risk of accumulating said microbubbles downstream of the treatment site.

59. The method of claim 58, wherein said half-life is less than thirty seconds.

60. The method of claim 58, wherein said half-life is less than twenty seconds.

61. The method of claim 58, wherein said half-life is a value in the range from five to ten seconds.

62. A system for treating a treatment site in a patient, said system comprising:
a catheter configured to be inserted into the patient;
a microfluidics device within said catheter; and;
microbubbles; wherein said microfluidics device is configured to focus gas and liquid streams at a nozzle to generate said microbubbles for delivery out of said catheter and toward the treatment site in the patient; and
an ultrasonic energy device configured to apply ultrasonic energy to the microbubbles to vibrate the microbubbles.

63. The system of claim 62, wherein the microbubbles are designed such that at least fifty percent of the microbubbles dissolve, without application of the ultrasonic energy, within one hundred twenty seconds after production of the microbubbles.

64. The system of claim 62, wherein the microbubbles are designed such that all of the microbubbles dissolve, without application of the ultrasonic energy, within ninety seconds after production of the microbubbles.

65. The system of claim 62, wherein the microbubbles are designed such that at least 30 percent of the microbubbles dissolve, without application of the ultrasonic energy, within 120 seconds after production of the microbubbles.

66. The system of claim 62, wherein the microbubbles are designed such that at least 90 percent of the microbubbles dissolve, without application of the ultrasonic energy, within 120 seconds after production of the microbubbles.

67. The system of claim 62, wherein the microbubbles are designed such that the microbubbles reduce in size by at least 50 percent, without application of the ultrasonic energy, within 120 seconds after production of the microbubbles.

68. The system of claim 62, wherein the microbubbles are designed such that the microbubbles reduce in size by at least 30 percent, without application of the ultrasonic energy, within 120 seconds after production of the microbubbles.

69. The system of claim 62, wherein the microbubbles are designed such that the microbubbles reduce in size by at least 90 percent, without application of the ultrasonic energy, within 120 seconds after production of the microbubbles.

70. The system of claim 62, wherein the microbubbles are designed such that at least 80 percent of a total volume of the microbubbles vanishes, without application of the ultrasonic energy, after a time period in the range of from 30 seconds to 180 seconds after production of the microbubbles.

71. The system of claim 62, wherein the microbubbles are designed such that at least 80 percent of the total volume of microbubbles vanishes, without application of the ultrasonic energy, after 120 seconds after production of the microbubbles.

72. The system of claim 62, wherein the microbubbles are designed such that at least 50 percent of a total volume of the microbubbles vanishes, without application of the ultrasonic energy, after a time period in the range of from 30 seconds to 180 seconds after production of the microbubbles.

73. The system of claim 72, wherein the microbubbles are designed such that at least 50 percent of the total volume of the microbubbles vanishes, without application of the ultrasonic energy, after 120 seconds after production of the microbubbles.

74. The system of claim 62, wherein the microbubbles are designed such that at least 30 percent of a total volume of the microbubbles vanishes, without application of the ultrasonic energy, after a time period in the range of from 30 seconds to 180 seconds after production of the microbubbles.

75. The system of claim 74, wherein the microbubbles are designed such that at least 30 percent of the total volume of the microbubbles vanishes, without application of the ultrasonic energy, after 120 seconds after production of the microbubbles.

76. The system of claim 62, wherein the microbubbles are designed such that at least 90 percent of the microbubbles dissolve, without application of the ultrasonic energy, after a time period in the range of 30 seconds to 180 seconds after production of the microbubbles.

77. The system of claim 62, wherein the microbubbles are designed such that at least 80 percent of the microbubbles dissolve, without application of the ultrasonic energy, after a time period in the range of 30 seconds to 180 seconds after production of the microbubbles.

78. The system of claim 62, wherein the microbubbles are designed such that at least 30 percent of the microbubbles dissolve, without application of the ultrasonic energy, after a time period in the range of 30 seconds to 180 seconds after production of the microbubbles.

79. The system of claim 62, wherein the microbubbles are designed such that at least 50 percent of the microbubbles dissolve, without application of the ultrasonic energy, within a predetermined time period after production of the microbubbles, wherein said predetermined time period is in the range of 30 seconds to 180 seconds.

80. The system of claim 62, wherein the microbubbles have an average diameter greater than or equal to about eight micrometers.

81. The system of claim 62, wherein the microbubbles have an average diameter greater than or equal to about twenty-five micrometers.

82. The system of claim 81, wherein said average diameter is in the range of twenty-five to thirty five micrometers.

83. The system of claim 62, wherein the microbubbles have an average diameter in the range of about eight micrometers to about twenty-five micrometers.

84. The system of claim 62, wherein the microbubbles have an average diameter in the range of about ten micrometers to about twenty micrometers.

85. The system of claim 62, wherein the microbubbles have an average diameter in the range of about eight micrometers to about twenty micrometers.

86. The system of claim 62, wherein the microbubbles are polydisperse, having a range of different diameter sizes, ranging from about one micrometer to about 100 micrometers.

87. The system of claim 86, wherein said range is from about one micrometer to about 30 micrometers.

88. The system of claim 86, wherein said range is from about five micrometers to about 100 micrometers.

89. The system of claim 62, wherein said microbubbles comprise an unstable shell formulation that includes one or more of: (1) a protein-based surfactant that is not cross-linked; (2) a lipid-based surfactant used above the melt temperature (Tm) of the lipid; (3) a lipid-based surfactant that is comprised of lipids with a single hydrophobic tail; and/or (4) a lipid-based surfactant with no pegylation.

90. The system of claim 62, wherein the microbubbles each have a shell and a core, wherein said core comprises an unstable gas.

91. The system of claim 90, wherein said core further comprises a stable gas.

92. The system of claim 91, wherein said core further comprises a neuroprotective gas.

93. The system of claim 90, wherein said core further comprises a neuroprotective gas.

94. The system of claim 62, wherein the treatment site is in the brain of the patient and the ultrasonic energy device is configured to apply ultrasound energy from outside the patient's body, trans-cranially to the microbubbles.

95. The system of claim 62, wherein the treatment site is in a cerebral artery and the catheter is configured and dimensioned to be inserted into the cerebral artery.

96. The system of claim 62, wherein the treatment site is in a femoral vein and the catheter is configured and dimensioned to be inserted into the femoral vein.

97. The system of claim 62, wherein the treatment site is in an iliofemoral vein and the catheter is configured and dimensioned to be inserted into the iliofemoral vein.

98. The system of claim 62, wherein the treatment site is in a popliteal vein and the catheter is configured and dimensioned to be inserted into the popliteal vein.

99. The system of claim 62, wherein the treatment site is in an iliac vein and the catheter is configured and dimensioned to be inserted into the iliac vein.

100. The system of claim 62, wherein the treatment site is in an inferior vena cava and the catheter is configured and dimensioned to be inserted into the inferior vena cava.

101. The system of claim 62, wherein the treatment site is in an axillary vein and the catheter is configured and dimensioned to be inserted into the axillary vein.

102. The system of claim 62, wherein the treatment site is in a subclavian vein and the catheter is configured and dimensioned to be inserted into the subclavian vein.

103. The system of claim 62, wherein the treatment site is in the microvasculature, having caused microvascular obstruction (MVO), and the catheter is configured and dimensioned to be inserted into an artery that feeds the microvasculature having been obstructed.

104. The system of claim 62, further comprising a delivery tube configured to deliver a thrombolytic agent toward the treatment site.

105. The system of claim 62, further comprising a thrombolytic agent to be applied to the treatment site.

106. The system of claim 62, wherein said catheter comprises a delivery channel extending from a distal end of said catheter and configured to deliver a thrombolytic agent from a distal end portion of said catheter toward the treatment site.

107. The system of claim 106, further comprising said thrombolytic agent in said delivery channel.

108. The system of claim 62, wherein said microfluidics device comprises a microfluidics flow-focusing device configured to generate said microbubbles.

109. The system of claim 108, wherein said microfluidics flow-focusing device is flexible and capable of being deformed for insertion into said catheter.

110. The system of claim 109, wherein said microfluidics flow-focusing device comprises a lamination of polymer layers and can be rolled up to be received within a cylindrical void of said catheter.

111. The system of claim 108, wherein said microfluidics flow-focusing device is rigid and comprises glass.

112. The system of claim 108, wherein said microfluidics flow-focusing device comprises electrodes configured to operate as a micro Coulter device to measure changes in impedance as the microbubbles flow past the electrodes.

113. The system of claim 108, wherein said microfluidics flow-focusing device comprises at least one liquid input channel, a gas input channel, and electrodes positioned in said gas input channel and at least one of said at least one liquid input channel, said electrodes being configured to detect electrical conductivity.

114. The system of claim 108, wherein said microfluidics device further comprises at least one sensor configured for real-time monitoring at least one of production rate and size of microbubbles produced.

115. The system of claim 114, wherein said at least one sensor comprises multiple non-polarizing electrodes.

116. The system of claim 115, wherein said at least one sensor comprises multiple optical waveguides.

117. The system of claim 114, wherein said real-time monitoring is performed in an automatic feedback loop, said system further comprising an automatic control system configured to automatically adjust at least one of gas pressure, gas flow rate, liquid pressure and liquid flow rate to maintain stable production rate and size of the microbubbles.

118. The system of claim 62, wherein said microfluidics device comprises a microfluidics T-junction device configured to produce said microbubbles.

119. The system of claim 62, wherein said microfluidics device comprises a microfluidics co-flow device configured to generate said microbubbles.

120. The system of claim 62, wherein said ultrasonic energy device comprises a transducer contained within said catheter.

121. The system of claim 120, wherein the treatment site is in the brain of the patient and said catheter and transducer are configured and dimensioned to be inserted into a blood vessel in the brain.

122. The system of claim 121, wherein the blood vessel is a cerebral artery.

123. The system of claim 120, wherein said transducer comprises one or more transducers configured for ultrasonic imaging as well as for said applying ultrasonic energy to vibrate said microbubbles.

124. The system of claim 62, further comprising a tube in fluid communication with and extending distally from a distal tip of said catheter;
  wherein said catheter has a first outside diameter and said tube has a second outside diameter, said second outside diameter being less than said first outside diameter; and
  wherein said tube is configured and dimensioned to deliver said microbubbles distally of said catheter.

125. The system of claim 124, wherein said tube is configured and dimensioned to deliver said microbubbles into a vessel that is too small for said catheter to be inserted into.

126. The system of claim 62, further comprising at least one sensor configured for real-time monitoring at least one of production rate and size of microbubbles produced.

127. The system of claim 62, wherein the treatment site comprises a blood clot, said system further comprising a thrombectomy device to assist in breaking up the blood clot.

128. The system of claim 62, wherein a blood clot is located at the treatment site.

129. The system of claim 62, wherein the microbubbles need only to survive a few seconds before delivery to the treatment site.

130. The system of claim 62, wherein said microbubbles have a half-life less than three minutes and are designed to dissolve within a short time after production, whether or not ultrasonic energy is applied, said time being sufficiently short to reduce the risk of accumulating said microbubbles downstream of the treatment site.

131. The system of claim 130, wherein said half-life is less than thirty seconds.

132. The system of claim 130, wherein said half-life is less than twenty seconds.

133. The system of claim 130, wherein said half-life is a value in the range from five to ten seconds.

134. A method of treating a blood clot, said method comprising:
- inserting a catheter into a patient;
- delivering low stability microbubbles from a microfluidics device within the catheter toward the blood clot in the patient, wherein the microfluidics device is configured to focus gas and liquid streams at a nozzle to generate said microbubbles for delivery out of said catheter and toward the blood clot;
- real-time monitoring at least one of production rate and size of microbubbles produced, wherein said real-time monitoring is performed in an automatic feedback loop;
- automatically adjusting at least one of gas pressure, gas flow rate, liquid pressure and liquid flow rate to maintain stable production rate and size of the microbubbles; and
- applying ultrasonic energy to the microbubbles to vibrate the microbubbles.

135. The method of claim 134, further comprising delivering a thrombolytic agent toward the blood clot.

136. A system for treating a blood clot, said system comprising:
- a catheter configured to be inserted into a patient;
- low stability microbubbles; a microfluidics device within said catheter configured to focus gas and liquid streams at a nozzle to generate said microbubbles for delivery out of said catheter and toward the blood clot in the patient and
- an ultrasonic energy device configured to apply ultrasonic energy to the microbubbles to vibrate the microbubbles;
- wherein said system further comprises at least one sensor configured for real-time monitoring at least one of production rate and size of microbubbles produced; and
- wherein said real-time monitoring is performed in an automatic feedback loop, said system further comprising an automatic control system configured to automatically adjust at least one of gas pressure, gas flow rate, liquid pressure and liquid flow rate to maintain stable production rate and size of the microbubbles.

\* \* \* \* \*